(12) United States Patent
Kanno et al.

(10) Patent No.: US 6,200,933 B1
(45) Date of Patent: Mar. 13, 2001

(54) 6-(NONSUBSTITUTED OR SUBSTITUTED) PHENOXY PICOLINIC ACIDS, PROCESS OF PREPARING THE SAME, AND AGRICULTURAL/HORTICULTURAL GERMICIDES CONTAINING THE SAME

(75) Inventors: Hisashi Kanno; Yoichi Kanda; Kazuhiko Sunagawa; Takayoshi Eizuka, all of Iwaki (JP)

(73) Assignee: Kureha Kagaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/331,734
(22) PCT Filed: Dec. 25, 1997
(86) PCT No.: PCT/JP97/04836
§ 371 Date: Aug. 9, 1999
§ 102(e) Date: Aug. 9, 1999
(87) PCT Pub. No.: WO98/29391
PCT Pub. Date: Jul. 9, 1998

(30) Foreign Application Priority Data

Dec. 26, 1996 (JP) .................................... 8-357062

(51) Int. Cl.$^7$ .................................... A01N 43/40
(52) U.S. Cl. .................... 504/244; 504/260; 546/326; 546/327
(58) Field of Search .................... 546/326, 327; 504/244, 255, 260

(56) References Cited

U.S. PATENT DOCUMENTS

| | | | |
|---|---|---|---|
| 3,940,403 | 2/1976 | Maeda et al. | 260/294.8 G |
| 3,994,908 | 11/1976 | Maeda et al. | 260/295 R |
| 4,826,531 | 5/1989 | Anthony et al. | 71/94 |
| 5,384,305 | 1/1995 | Foster et al. | 504/130 |

FOREIGN PATENT DOCUMENTS

| | | |
|---|---|---|
| 0 488 474 A1 | 6/1992 | (EP) . |
| 0 882 175 A1 | 12/1998 | (EP) . |
| 73.17359 | 12/1973 | (FR) . |
| 49-11885 | 2/1974 | (JP) . |
| 4-290805 | 10/1992 | (JP) . |

OTHER PUBLICATIONS

Kanno, H. et al, "Preparation of novel N–(unsubstituted or substituted0–4substituted–6–thiocarboxamides, processes for producing the same, and herbices" CA 127:135725, 1997.*

March Advanced Organic Chemistry 3$^{rd}$ edition Wiley Interscience Publication 1985 pp 788–789.

March, Jerry "Advanced Organic Chemistry" third edition (United States of America) A Wiley Interscience Publication (1985) p. 788–789 (Refer to "6–5 Hydrolysis of Nitriles").

* cited by examiner

Primary Examiner—Amelia Owens
(74) Attorney, Agent, or Firm—Nixon & Vanderhye

(57) ABSTRACT

An agricultural or horticultural fungicide containing 6-(unsubstituted or substituted) phenoxy picolinic acid represented by the general formula (I), as an effective ingredient.

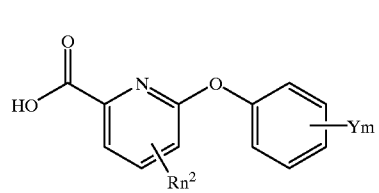

(I)

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^2$ is an integer of 0 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^2$ are not less than 2, Rs and Ys may be the same or different, respectively.

The compound is useful as an effective ingredient of agricultural or horticultural fungicides.

5 Claims, No Drawings

6-(NONSUBSTITUTED OR SUBSTITUTED) PHENOXY PICOLINIC ACIDS, PROCESS OF PREPARING THE SAME, AND AGRICULTURAL/HORTICULTURAL GERMICIDES CONTAINING THE SAME

TECHNICAL FIELD

The present invention relates to 6-(unsubstituted or substituted) phenoxy picolinic acid, a process for producing the compound and an agricultural or horticultural fungicide containing the compound.

BACKGROUND ART

Certain kinds of 6-(unsubstituted or substituted) phenoxy picolinic acids have been described in Japanese Patent Applications Laid-open (KOKAI) Nos. 4-290805(1992), 4-217959(1992) or the like. However, in these prior arts, it has been only described that these compounds having a pyridine ring whose 3- to 5-positions are unsubstituted are usable as intermediates of herbicides. Therefore, there have been no descriptions concerning a fungicidal or germicidal activity of these compounds.

On the other hand, it has been demanded to provide compounds which are useful as agricultural or horticultural fungicides, and can show a low toxicity to human and cattle, a high safety upon handling and excellent control effects on extensive diseases of plants.

DISCLOSURE OF THE INVENTION

The present invention have been made in order to solve the above problems. It is an object of the present invention to provide an agricultural or horticultural fungicide which can exhibit a low toxicity to human and cattle, a high safety upon handling and an excellent control effect on extensive diseases of plants.

As a result of various studies by the present inventors for developing novel industrially useful pyridine derivatives, it has been found that 6-(unsubstituted or substituted) phenoxy picolinic acid has an excellent fungicidal or germicidal effect. The present invention has been attained on the basis of this finding.

That is, in a first aspect of the present invention, there is provided 6-(unsubstituted or substituted) phenoxy picolinic acid represented by the general formula (I-a):

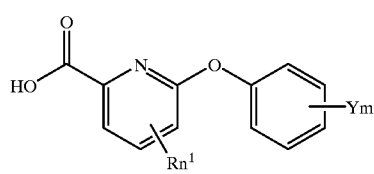

(I-a)

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^1$ is an integer of 1 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^1$ are not less than 2, Rs and Ys may be the same or different, respectively.

In a second aspect of the present invention, there is provided a process for producing 6-(unsubstituted or substituted) phenoxy picolinic acid represented by the general formula (I-b), which process comprises metallizing a 2-halogeno-6-(unsubstituted or substituted) phenoxy pyridine derivative represented by the general formula (III) to obtain 2-(metal-substituted)-6-(unsubstituted or substituted) phenoxy pyridine derivative represented by the general formula (II), reacting the obtained pyridine derivative (II) with carbon dioxide, and then subjecting the reaction product to proton-substitution.

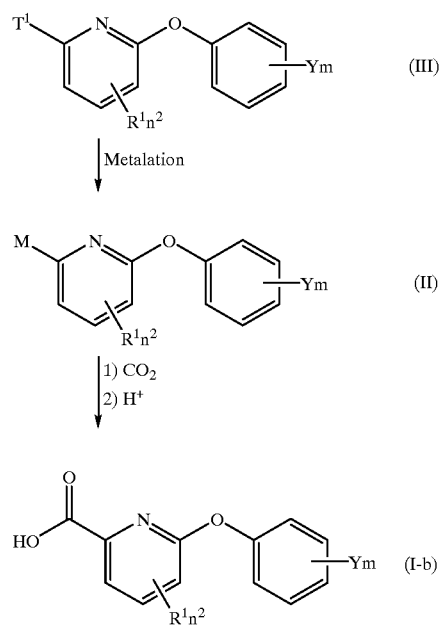

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a di($C_1$ to $C_4$) alkylamino group or a $C_7$ to $C_8$ aralkyl($C_1$ to $C_4$ alkyl)amino group;

$n^2$ is an integer of 0 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m and $n^2$ are not less than 2, $R^1$s and Ys may be the same or different, respectively;

$T^1$ is a halogen atom; and

M is alkali metal, alkali earth metal-Q (wherein Q is a halogen atom), or ½(Cu-alkali metal).

In a third aspect of the present invention, there is provided a process for producing 6-(unsubstituted or substituted) phenoxy picolinic acid represented by the general formula (I-a), which process comprises hydrolyzing a 2-cyano-6-(unsubstituted or substituted) phenoxy pyridine derivative represented by the general formula (IV).

$$\text{(IV)}$$

[Structure: NC-pyridine-O-phenyl with Ym, Rn¹ substituents]

↓ Hydrolysis $$\text{(I-a)}$$

[Structure: HOOC-pyridine-O-phenyl with Ym, Rn¹ substituents]

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^1$ is an integer of 1 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^1$ are not less than 2, Rs and Ys may be the same or different, respectively.

In a fourth aspect of the present invention, there is provided a process for producing 6-(unsubstituted or substituted) phenoxy picolinic acid represented by the general formula (I-a), which process comprises hydrolyzing a 6-(unsubstituted or substituted) phenoxy picolinic acid ester represented by the general formula (V).

$$\text{(V)}$$

[Structure: BOOC-pyridine-O-phenyl with Ym, Rn¹ substituents]

↓ Hydrolysis $$\text{(I-a)}$$

[Structure: HOOC-pyridine-O-phenyl with Ym, Rn¹ substituents]

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^1$ is an integer of 1 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m and $n^1$ are not less than 2, Rs and Ys may be the same or different, respectively; and B is a lower alkyl group.

In a fifth aspect of the present invention, there is provided an agricultural or horticultural fungicide containing 6-(unsubstituted or substituted) phenoxy picolinic acid represented by the general formula (I), as an effective ingredient.

$$\text{(I)}$$

[Structure: HOOC-pyridine-O-phenyl with Ym, Rn² substituents]

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl) amino group or a $C_7$ to $C_8$ aralkyl($C_1$ to $C_4$ alkyl)amino group;

$n^2$ is an integer of 0 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^2$ are not less than 2, Rs and Ys may be the same or different, respectively.

The present invention will be described in detail below.

First, the 6-(unsubstituted or substituted) phenoxy picolinic acid represented by the above general formula (I) (hereinafter referred to merely as "the present compound (I)", is explained.

Examples of the halogen atoms as R of the present compound (I) may include a fluorine atom, a chlorine atom, a bromine atom or the like; as the $C_1$ to $C_4$ alkyl groups, there may be exemplified methyl, ethyl, propyl, isopropyl or the like; as the $C_1$ to $C_4$ haloalkyl groups, there may be exemplified trifluoromethyl, trichloromethyl or the like; as the $C_1$ to $C_4$ alkoxy groups, there may be exemplified methoxy, ethoxy, (1-methyl)ethoxy or the like; as the $C_1$ to $C_4$ haloalkoxy groups, there may be exemplified difluoromethoxy, trifluoromethoxy, 2,2,2-trifluoroethoxy or the like; as the $C_1$ to $C_4$ alkylthio groups, there may be exemplified methylthio, ethylthio or the like; as the $C_1$ to $C_4$ alkylamino groups, there may be exemplified methylamino, ethylamino or the like; as the di($C_1$ to $C_4$ alkyl)amino groups, there may be exemplified dimethylamino, ethylmethylamino or the like; and as the $C_7$ to $C_8$ aralkyl($C_1$ to $C_4$ alkyl)amino groups, there may be exemplified phenylmethyl (methyl)amino, phenylmethyl(ethyl)amino or the like.

The above-specified substituents for R of the present compound (I) are identically usable as those specific substituents for R of the above compound (I-a) and $R^1$ of the above compound (I-b) as described hereinbefore, as well as $R^2$ of a compound (I-c) and $R^3$ of a compound (I-d) as described in detail hereinafter.

With respect to the substituent Y of the present compound (I), as the halogen atoms, there may be exemplified a fluorine atom, a chlorine atom, a bromine atom or the like; as the $C_1$ to $C_4$ alkyl groups, there may be exemplified methyl, ethyl, (1-methyl)ethyl or the like; as the $C_1$ to $C_4$ alkoxy groups, there may be exemplified methoxy, ethoxy, (1-methyl)ethoxy or the like; as the $C_1$ to $C_4$ alkylthio groups, there may be exemplified methylthio, ethylthio, (1-methyl)ethylthio or the like; as the $C_1$ to $C_4$ haloalkyl groups, there may be exemplified trifluoromethyl or the like;

as the $C_1$ to $C_4$ haloalkoxy groups, there may be exemplified trifluoromethoxy, difluoromethoxy or the like; and as the $C_1$ to $C_4$ haloalkylthio groups, there may be exemplified trifluoromethylthio, difluoromethylthio or the like.

The m of the present compound (I) is usually an integer of 0 to 5, preferably an integer of 0 to 2, more preferably 1.

It is especially preferred that at least one of Ym is bonded to the 3-position of the phenoxy ring. The above definition of the preferred Ym is similarly applied to the Ym of the compounds (I-a) to (I-d).

Meanwhile, symbols used in two or more chemical formulae, such as Y and m, have the same definitions or meanings as those used in the present compound (I). The other symbols used in two or more chemical formulae also have the same definitions or meanings.

The $n^2$ of the present compound (I) is usually an integer of 0 to 3, preferably an integer of 0 to 1, more preferably 1.

The above definition of the $n^2$ is similarly applied to the $n^1$ of the compound (I-a) and the $n^2$ of the compound (I-b) as described hereinbefore, as well as the $n^1$ of the compound (I-c) and the $n^1$ of the compound (I-d) as described in detail hereinafter.

It is still preferred that at least one of $Rn^2$ is bonded to the 4-position of the pyridine ring. The above definition of the preferred $Rn^2$ is similarly applied to the $Rn^1$ of the compound (I-a) and the $R^1n^2$ of the compound (I-b), as well as the $R^2n^1$ of the compound (I-c) and the $R^3n^1$ of the compound (I-d).

As the $T^1$ of the compound (III), there may be exemplified halogen atoms such as fluorine, chlorine, bromine or iodine. Among these halogen atoms, chlorine and bromine are preferred.

The definition of the above $T^1$ is similarly applied to the $T^2$ of the compound (VI) as described hereinafter.

As the present compounds (I) in which the above-mentioned preferred substituents and integers are combined, there may be exemplified those shown in Tables 1 to 3.

TABLE 1

| Compound | Substituent | |
|---|---|---|
| No. | $Rn^{2a)}$ | $Ym^{b)}$ |
| I-1 | 4-OCH$_3$ | 3-CF$_3$ |
| I-2 | 4-OCH$_3$ | 3-OCF$_3$ |
| I-3 | 4-OCH$_3$ | 3-SCF$_3$ |
| I-4 | 4-OCH$_3$ | 3-OCHF$_2$ |
| I-5 | 4-CH$_3$ | 3-CF$_3$ |
| I-6 | 4-Cl | 3-CF$_3$ |
| I-7 | 4-N(CH$_3$)$_2$ | 3-CF$_3$ |
| I-8 | 4-SCH$_3$ | 3-CF$_3$ |
| I-9 | 4-NCH$_3$(CH$_2$Ph) | 3-CF$_3$ |
| I-10 | 4-NHCH$_3$ | 3-CF$_3$ |
| I-11 | 3-Cl | 3-CF$_3$ |
| I-12 | 5-OCH$_3$ | 3-CF$_3$ |
| I-13 | — | 3-CF$_3$ |
| I-14 | — | 3-OCF$_3$ |
| I-15 | — | 4-CH$_3$ |
| I-16 | — | 3-CH$_3$ |
| I-17 | — | 2-CH$_3$ |
| I-18 | — | 4-OCH$_3$ |
| I-19 | — | 3-Cl |

TABLE 2

| Compound | Substituent | |
|---|---|---|
| No. | $Rn^{2a)}$ | $Ym^{b)}$ |
| I-20 | — | — |
| I-21 | — | 3-SCH$_3$ |
| I-22 | 4-OCH$_2$CF$_3$ | 3-CF$_3$ |
| I-23 | 4-OCH$_3$ | — |
| I-24 | 4-OCH$_3$ | 3-OCH$_3$ |
| I-25 | 4-OCH$_3$ | 3-SCH$_3$ |
| I-26 | 4-OCH$_3$ | 3-CH$_3$ |
| I-27 | 4-OCH$_3$ | 3-Cl |
| I-28 | 4-OCH$_3$ | 3-Br |
| I-29 | 4-OCH$_2$CH$_3$ | 3-CH$_3$ |
| I-30 | 4-NCH$_2$CH$_3$(CH$_2$Ph) | 3-CF$_3$ |
| I-31 | 4-NHC$_2$CH$_3$ | 3-CF$_3$ |
| I-32 | 4-CF$_3$ | 3-CF$_3$ |

TABLE 3

| Compound | Substituent | |
|---|---|---|
| No. | $Rn^{2a)}$ | $Ym^{b)}$ |
| I-33 | 4-OCH$_3$ | 2-Cl, 5-CF$_3$ |
| I-34 | 4-OCH$_3$ | 2-F, 3-CF$_3$ |
| I-35 | 4-OCH$_3$ | 3-CF$_3$, 4-Cl |
| I-36 | 4-OCH$_3$ | 3-F, 5-CF$_3$ |
| I-37 | 4-OCH$_3$ | 2-F, 5-CF$_3$ |
| I-38 | 4-OCH$_3$ | 3,5-Cl$_2$ |
| I-39 | 5-OCHF$_2$ | 3-CF$_3$ |

Note:
a) R represents a substituent bonded to the pyridine ring; for example, 4-OCH$_3$ of the compound No. (I-1) indicates that OCH$_3$ is bonded to a carbon atom located at the 4-position of the pyridine ring.
b) Y represents a substituent bonded to the phenoxy ring; for example, 3-CF$_3$ of the compound No. (I-1) indicates that CF$_3$ is bonded to a carbon atom located at the 3-position of the phenoxy ring. Further, "2-Cl, 5-CF$_3$," of the compound No. (I-33) indicates that Cl is bonded to a carbon atom located at the 2-position of the phenoxy ring, and CF$_3$ is bonded to a carbon atom located at the 5-position of the phenoxy ring.

Next, the process for producing the present compound (I) is explained. In the production processes according to the second through fourth aspects of the present invention, as solvents used therein, there may be usually exemplified aromatic hydrocarbons such as benzene, toluene, xylene, methyl naphthalene or the like; aliphatic hydrocarbons such as petroleum ethers, pentane, hexane, heptane, methyl cyclohexane or the like; halogenated hydrocarbons such as methylene chloride, chloroform, carbon tetrachloride, chlorobenzene or the like; amides such as dimethyl formamide, dimethyl acetamide, N-methyl-2-pyrrolidinone or the like; ethers such as diethyl ether, dimethoxy ethane, diisopropyl ether, tetrahydrofuran, diethylene glycol dimethyl ether (DIGLYM), dioxane or the like; or alcohols such as methanol, ethanol or the like.

As other solvents usable in the present invention, there may be exemplified water, carbon disulfide; acetonitrile; ethyl acetate; acetic anhydride; pyridine; dimethyl sulfoxide; hexamethyl phosphoric amide or the like. These solvents may be used in the form of a mixture of any two or more thereof. All individual reaction steps of the production processes according to the present invention can be advantageously carried out in the presence of either a solvent or a mixed solvent. In addition, there may also be used a solvent composition composed of solvents which are incapable of forming a uniform layer when mixed with each other. In the case where such a solvent composition is used, it is adequate to add to the reaction system a phase transfer catalyst, for example, ordinarily used quaternary ammonium salt or crown ether.

Further, in the case where a base is used in production or separation steps of the processes according to the second through fourth aspects of the present invention, as such bases, there may be usually exemplified the following basic compounds:

Alkali metals such as lithium, sodium, potassium or the like, and alkali earth metals such as magnesium or the like;

alkali metal alkoxides such as sodium methoxide, sodium ethoxide, potassium t-butoxide or the like;

alkali metal hydrides such as sodium hydride, potassium hydride or the like;

alkali metal carbonates such as potassium carbonate, sodium carbonate or the like;

alkali earth metal carbonates such as calcium carbonate, barium carbonate or the like;

alkali earth metal hydrides such as calcium hydride or the like;

alkali metal hydroxides such as sodium hydroxide, potassium hydroxide or the like;

alkali earth metal hydroxides such as calcium hydroxide, magnesium hydroxide or the like;

alkali earth metal oxides such as magnesium oxide, calcium oxide or the like;

organic alkali metal compounds such as methyl lithium, ethyl lithium, n-butyl lithium, phenyl lithium or the like;

organic Grignard reagents such as methyl magnesium iodide, ethyl magnesium bromide, n-butyl magnesium bromide or the like;

organic copper compounds prepared by reacting organic alkali metal compounds or Grignard reagents with monovalent copper salts; or alkali metal amides such as lithium diisopropylamide or the like.

Next, the respective production processes according to the present invention, are described.

The production process according to the second aspect of the present invention, is explained. This production process comprises substituting the halogen atom ($T^1$) of the compound represented by the general formula (III) with a metal to obtain the metallized compound represented by the general formula (II), and then forming a carbon-to-carbon bond between the metallized carbon atom of the obtained metallized compound (II) and the carbon atom of carbon dioxide (hereinafter referred to merely as "step A").

That is, the present compound (I-b) can be produced by metallizing a 2-halogeno-6-(unsubstituted or substituted) phenoxy pyridine derivative represented by the general formula (III) (hereinafter referred to merely as a "compound (III)") to obtain a 2-(metal-substituted)-6-(unsubstituted or substituted) phenoxy pyridine derivative represented by the general formula (II) (hereinafter referred to merely as a "compound (II)"), reacting the compound (II) with carbon dioxide, and then substituting a proton for the metal.

The above reaction can be shown by the following reaction formula:

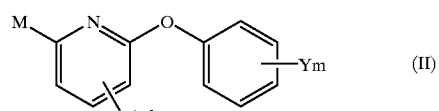

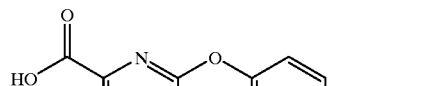

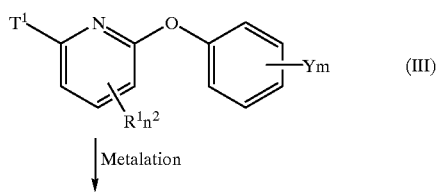

wherein $R^1$, Y, m, $n^2$, $T^1$ and M have the same definitions as described above.

The above-mentioned compound (II) can be produced by treating the compound (III) with a metallizing agent.

As the metallizing agents, there may be usually exemplified organic alkali metal compounds such as butyl lithium, methyl lithium, phenyl lithium or the like; alkali metals such as lithium, sodium, potassium or the like; or alkali earth metals such as magnesium or the like. In addition, as the metallizing agents, there may also be used organic copper compounds produced by reacting an organic alkali metal compound prepared in the presence of the above-mentioned reagents, or a Grignard reagent, with a monovalent-copper salt.

The amount of the metallizing agent used is usually 0.5 to 3 moles, preferably 0.8 to 1.5 moles based on one mole of the compound (III). The carbon dioxide may be used in not less than an equivalent amount up to in an extremely excessive amount.

The temperature for carrying out the treatment using the metallizing agent and the reaction with carbon dioxide is usually −100° C. to 100° C., preferably −80° C. to 80° C. The reaction time is from several seconds to several hours, preferably from one minute to 5 hours.

The present compound (I-b) can be produced by reacting the obtained compound (II) with carbon dioxide, and then subjecting the reaction product to proton-substitution. The above proton-substitution may be conducted by treating the reaction solution with an aqueous acid solution. As the acids, there may be usually exemplified inorganic acids such as hydrochloric acid, hydrobromic acid, hydroiodic acid, perchloric acid, sulfuric acid or the like; or organic acids such as formic acid, acetic acid, p-toluene sulfonic acid or the like. These acids may be used in the form of a mixture of any two or more thereof.

As solvents used in the production of the present compound (I-b), there may be exemplified such solvents which are inert to the organic metal compounds. Examples of the solvents may include aliphatic hydrocarbons such as petroleum ethers, pentane, hexane, heptane, methyl cyclohexane or the like; ethers such as diethyl ether, dimethoxy ethane, diisopropyl ether, tetrahydrofuran, diethylene glycol dimethyl ether (DIGLYM), dioxane or the like; or aromatic hydrocarbons such as benzene, toluene, xylene, methyl naphthalene or the like. These solvents may be used in the form of a mixture of any two or more thereof.

The compound (III) used as a raw material in the step A, can be produced by nucleophilically substituting one of halogen atoms of a 2,6-dihalogeno pyridine derivative represented by the general formula (VI) (hereinafter referred to merely as a "compound (VI)") with a (substituted or unsubstituted) phenol represented by the general formula (VII) (hereinafter referred to merely as a "compound (VII)").

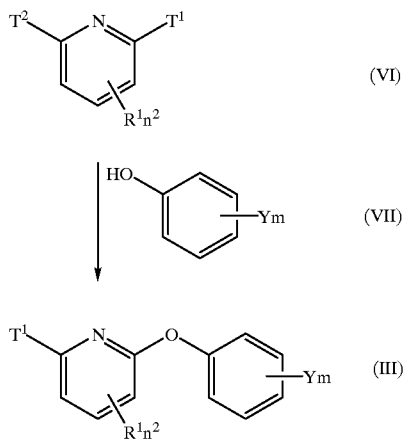

wherein $R^1$, Y, m, $n^2$ and $T^1$ have the same definitions as described above; $T^2$ is a halogen atom; and $T^1$ and $T^2$ may be the same or different.

The compound (III) as the reaction product still contains at least one other halogen atom which can be nucleophilically substituted (in the case where a halogen atom is bonded to the 4- position of the pyridine ring, the number of other halogen atoms remaining in the compound (III) become two in total). Therefore, from the standpoint of high yield of the compound (III), it is preferred that the phenoxylation reaction be inhibited at positions other than the aimed position.

Accordingly, the amounts of the compound (VII) and the base used are usually 0.5 to 1.5 moles, preferably 0.8 to 1.2 moles based on one mole of the compound (VI), respectively (in the present specification, the amount of the base used is represented as such an amount calculated as a base capable of capturing one hydrogen halide, for example, such as sodium hydride. The amount of the base used for nucleophilically substituting the halogen atom bonded to the pyridine ring with typically the below-described compounds (VII), is represented similarly. Usually, the amounts correspond to so-called equivalent amounts).

From the standpoint of facilitating the separation of the compound (III) as the reaction product, it is preferred that the amount of unreacted compound (VII) be reduced. Therefore, the compound (VII) may be used in an equimolar amount or in a slightly excessive amount based on the base.

The reaction temperature is usually 0 to 250° C., preferably 60 to 180° C. The reaction time is from several minutes to several days, preferably from 30 minutes to 2 days.

The compound (VI) as the above raw material may be produced in the following manner.

That is, among the 2,6-dihalogeno pyridine derivatives (VI), 2,6-dihalogeno-4-substituted pyridine can be produced by substituting a hydroxy group of 2-halogeno-4-substituted-6-hydroxy pyridine with a halogen atom using a halogenating agent such as phosphorus oxychloride or phosphorus oxybromide.

For instance, 2,6-dibromo-4-methyl pyridine [compound (VI): $T^1$=Br, $T^2$=Br and $Rn^2$=4-$CH_3$] can be produced by brominating a hydroxy group of 2-bromo-6-hydroxy-4-methyl pyridine in tribromomethane as a solvent using phosphorus oxybromide, as described in Japanese Patent Application Laid-Open (KOKAI) No. 6-40813(1994).

2,6-dihalogeno-4-($C_1$ to $C_4$ alkoxy, $C_1$ to $C_4$ haloalkoxy, $C_1$ to $C_4$ alkylthio, $C_1$ to $C_4$ alkylamino, di($C_1$ to $C_4$ alkyl)amino or $C_7$ to $C_8$ aralkyl($C_1$ to $C_4$ alkyl)amino) pyridine [compound (VI): $T^1$=halogen atom, $T^2$=halogen atom and Rm=4-($C_1$ to $C_4$ alkoxy, $C_1$ to $C_4$ haloalkoxy, $C_1$ to $C_4$ alkylthio, $C_1$ to $C_4$ alkylamino, di($C_1$ to $C_4$ alkyl) amino or $C_1$ to $C_4$ aralkyl($C_1$ to $C_4$ alkyl)amino)] can be produced by nucleophilically substituting a nitro group of corresponding 2,6-dihalogeno-4-nitro pyridine under a basic condition, as described in Japanese Patent Application Laid-Open (KOKAI) Nos. 6-40813(1994), 8-269055(1996) and the like. In addition, the dialkylamino compounds or the aralkyl(alkyl)amino compounds can be produced by the alkylation or aralkylation of the above-mentioned alkylamino compounds.

The 2,6-dihalogeno pyridine derivatives (VI) having substituents bonded to the 3- and/or 5-positions of the pyridine ring, can also be produced from compounds which can be obtained by known techniques. Examples of a part of these compounds are as follows:

3-chloro-2,6-dibromo pyridine and 2,6-dibromo-3-trifluoromethyl pyridine (DE 2,432,686);

2,6-dibromo-3-methoxy pyridine (Aust. J. Chem., 34(4), 927–32(1981));

3-dimethylamino-2,6-dibromo pyridine (J. Heterocycl. Chem., 22(4), 985–91(1985));

2,6-dibromo-3,5-dimethyl pyridine (Z. Chem., 28(2), 59–60(1988)); or the like.

In the case where different atoms (inclusive of hydrogen atom in addition to halogen atom as a substituent) are bonded to the 3- and 5-positions of the pyridine ring, the compound (III) produced upon the phenoxylation reaction is composed of a mixture of isomers. The isomers may be used immediately in the form of the mixture, or individually after being separated into the respective isomers.

As the above-mentioned compounds (VII), there may be used commercially available products or such compounds which can be produced by known techniques. Examples of these compounds are as follows:

Examples of Phenols

Phenol;
2-chlorophenol;
3-chlorophenol;
4-chlorophenol;
2-methylphenol;
3-methylphenol;
4-methylphenol;
2-methoxyphenol;
3-methoxyphenol;
4-methoxyphenol;
3-(methylthio)phenol;
2-(trifluoromethyl)phenol;
3-(trifluoromethyl)phenol;
4-(trifluoromethyl)phenol;
3-(trifluoromethoxy)phenol;
3-(difluoromethoxy)phenol;
3-(trifluoromethylthio)phenol;
2-chloro-5-(trifluoromethyl)phenol;
4-chloro-3-(trifluoromethyl)phenol;
2-fluoro-3-(trifluoromethyl)phenol;
2-fluoro-5-(trifluoromethyl)phenol;
3-fluoro-5-(trifluoromethyl)phenol;

3,5-dichlorophenol; and 3,5-di(trifluoromethyl)phenol.

The production process according to the third aspect of the present invention, is explained.

The present compound (I-a) can be produced by hydrolyzing a 2-cyano-6-(unsubstituted or substituted) phenoxy pyridine derivative represented by the general formula (IV) (hereinafter referred to merely as "step B").

The above reaction can be represented by the following reaction formula:

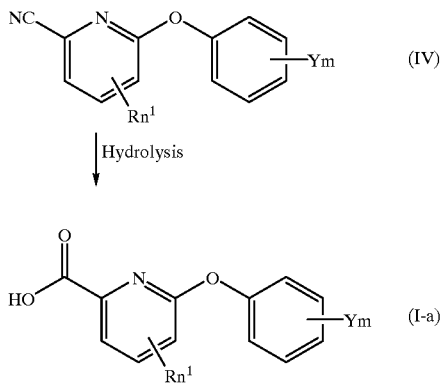

wherein R, Y, m and $n^1$ have the same definitions as described above.

The above-mentioned hydrolysis can be conducted under either acidic or basic condition. In the case where the hydrolysis is conducted under an acidic condition, as catalysts, there may be usually used inorganic acids such as hydrochloric acid, hydrobromic acid, sulfuric acid or the like, and as solvents, there may be usually used water, a mixed solution of water and an organic acid such as acetic acid or the like. In the case where the hydrolysis is conducted under a basic condition, as bases, there may be usually used alkali metal bases such as sodium hydroxide, potassium hydroxide or the like, and as solvents, there may be usually used water or a mixed solution of water and alcohols, etc.

The hydrolysis temperature is usually from 20° C. to the reflux point, preferably from 50° C. to the reflux point. The reaction time is from several minutes to several days, preferably from 30 minutes to one day.

The compound (IV) used as a raw material in the step B, can be produced by nucleophilically substituting a halogen atom of a 2-cyano-6-halogeno pyridine derivative represented by the general formula (VIII) (hereinafter referred to merely as a "compound (VIII)") with a (substituted or unsubstituted) phenol represented by the general formula (VII). The above reaction is represented by the following reaction formula:

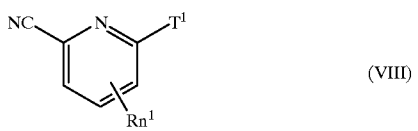

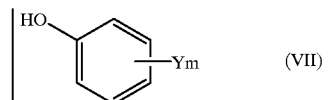

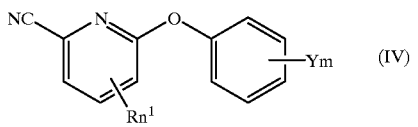

wherein R, Y, m and $n^1$ have the same definitions as described above; and $T^1$ is a halogen atom.

In the phenoxylation reaction of the compound (VIII), the compound (VIII) and the compound (VII) are reacted with each other usually in a solvent under a basic condition.

In the above reaction, in the case where no halogen atom is bonded to the 4-position of the pyridine ring of the compound (VIII), the compound (VII) may be charged to the reaction system in an amount of more than 2 moles based on one mole of the compound (VIII) in the presence of an excess amount of the base. The amount of the base used is usually 0.8 to 10 moles, preferably 1 to 5 moles based on one mole of the compound (VIII).

On the other hand, in the case where a halogen atom is bonded to the 4-position of the pyridine ring of the compound (VIII), from the standpoint of high yield of the compound (IV), it is preferred that the phenoxylation reaction be inhibited at positions other than the aimed position.

Accordingly, the compound (VII) and the base used are usually used in an amount of 0.5 to 1.5 moles, preferably 0.8 to 1.2 moles based on one mole of the compound (VIII), respectively.

Further, a catalyst such as copper halide may be added to the reaction system. The amount of the catalyst added is usually 0.01 to 100 moles, preferably 0.1 to 5 moles based on one mole of the compound (VIII). The reaction temperature is usually 0 to 200° C., preferably 60 to 180° C. The reaction time is usually from several minutes to several days, preferably from one hour to 2 days.

The above compound (VIII) may be produced in the following manner.

That is, among the 4-substituted compounds, 2-cyano-4,6-dichloro pyridine [compound (VIII): $T^1$=Cl and $Rn^1$=4-Cl] can be produced by chlorinating 2-cyano pyridine, as described in British Patent No. 1,301,724. By subjecting the thus obtained compound to nucleophilic substitution under a basic condition, 2-cyano-6-chloro-4-($C_1$ to $C_4$ alkoxy, $C_1$ to $C_4$ haloalkoxy, amino, $C_1$ to $C_4$ alkylamino or $C_1$ to $C_4$ alkylthio) pyridine can be produced. In addition, by reacting the amino compound and the $C_1$ to $C_4$ alkylamino compound with halogenated $C_1$ to $C_4$ alkyl and halogenated $C_7$ to $C_8$ aralkyl, respectively, under a basic condition, a di($C_1$ to $C_4$ alkyl)amino compound or a $C_1$ to $C_4$ alkyl($C_7$ to $C_8$ aralkyl)amino compound can be produced.

Among the 4-substituted compounds, 2-cyano-6-chloro-4-methyl pyridine [compound (VIII): $T^1$=Cl and $Rn^1$=4-$CH_3$] has been described in International Patent Application Laid-Open No. WO94/08991.

Among the 3-substituted compounds, 2-cyano-3,6-dichloro pyridine [compound (VIII): $T^1$=Cl and $Rn^1$=3-Cl]

has been described in specifications of Russian Patent No. 1,728,241 and U.S. Pat. No. 4,766,219.

2-cyano-3,6-dichloro pyridine [compound (VIII): $T^1$=Cl and $Rn^1$=3-Cl], 2-cyano-6-chloro-4-methyl pyridine [compound (VIII): $T^1$=Cl and $Rn^1$=4-$CH_3$], 2-cyano-6-chloro4-methoxy pyridine [compound (VIII): $T^1$=Cl and $Rn^1$=4-$OCH_3$], etc., can be produced by oxidizing corresponding 2-unsubstituted compounds into respective N-oxide compounds; alkylating each N-oxide compound to produce an N-alkoxy derivative; and then reacting the obtained derivative with sodium cyanide.

Next, the production process according to the fourth aspect of the present invention, is explained.

The present compound (I-a) can be produced by hydrolyzing a 6-(unsubstituted or substituted) phenoxy picolinic acid lower-alkyl ester derivative represented by the general formula (V) (hereinafter referred to merely as "step C"). The above reaction can be represented by the following reaction formula:

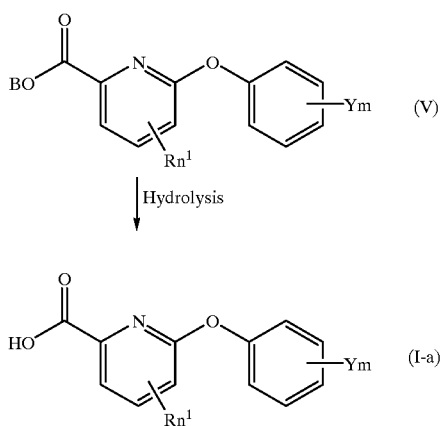

wherein R, Y, m, $n^1$ and B have the same definitions as described above.

As the lower alkyl groups B, there may be exemplified $C_1$ to $C_6$ alkyl groups such as methyl, ethyl, propyl, 1-methyl ethyl, butyl, pentyl, hexyl or the like. As the lower alkyl group B, there may be usually used methyl or ethyl.

The above-mentioned hydrolysis can be conducted under either acidic or basic condition. In the case where the hydrolysis is conducted under an acidic condition, as catalysts, there may be usually used inorganic acids such as hydrochloric acid, hydrobromic acid, sulfuric acid or the like, and as solvents, there may be usually used water, a mixture of water and an organic acid such as acetic acid, or the like. In the case where the hydrolysis is conducted under a basic condition, as bases, there may be usually used alkali metal bases such as sodium hydroxide, potassium hydroxide or the like, and as solvents, there may be usually used water or a mixed solution of water and alcohols, etc.

The hydrolysis temperature is usually from 20° C. to the reflux point, preferably from 50° C. to the reflux point. The reaction time is from several minutes to several days, preferably from 30 minutes to one day.

The compound (V) used as a raw material in the step C, can be produced by nucleophilically substituting a halogen atom of a 6-halogeno picolinic acid lower-alkyl ester derivative represented by the general formula (IX) (hereinafter referred to merely as a "compound (IX)") with the (substituted or unsubstituted) phenol represented by the general formula (VII). The above reaction is represented by the following reaction formula:

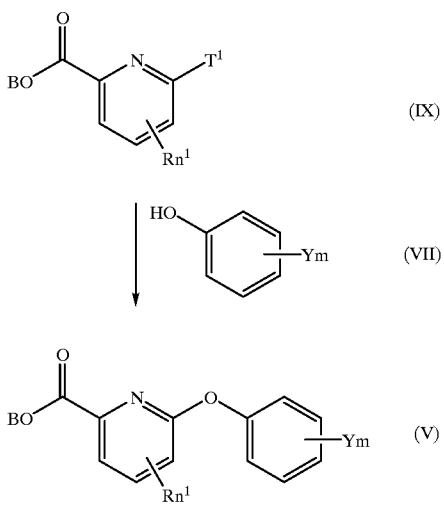

wherein R, Y, m, $n^1$ and B have the same definitions as described above; and $T^1$ is a halogen atom.

In the phenoxylation reaction of the compound (IX), the compound (IX) and the compound (VII) are reacted with each other usually in a solvent under a basic condition.

In the above reaction, in the case where no halogen atom is bonded to the 4-position of the pyridine ring of the compound (IX), the compound (VII) may be charged in an amount of more than 2 moles based on one mole of the compound (IX) in the presence of an excess amount of the base. The amount of the base used is usually 0.8 to 10 moles, preferably 1 to 5 moles based on one mole of the compound (IX).

The amount of the compound (VII) charged is usually 0.8 to 15 moles, preferably 1.2 to 10 moles based on one mole of the compound (IX).

On the other hand, in the case where a halogen atom is bonded to the 4-position of the pyridine ring of the compound (IX), from the standpoint of high yield of the compound (V), it is preferred that the phenoxylation reaction be inhibited at positions other than the aimed position.

Accordingly, the amount of the compound (VII) and the base used is usually 0.5 to 1.5 moles, preferably 0.8 to 1.2 moles based on one mole of the compound (IX), respectively.

Further, a catalyst such as copper halide may be added to the reaction system. The amount of the catalyst added is usually 0.01 to 10 moles, preferably 0.1 to 5 moles based on one mole of the compound (IX). The reaction temperature is usually 0 to 200° C., preferably 60 to 180° C. The reaction time is usually from several minutes to several days, preferably from one hour to 2 days.

Next, the above compound (IX) can be produced in the following manner.

That is, 4,6-dichloro picolinic acid lower-alkyl ester [compound (IX): $T^1$=Cl and $Rn^1$=4-Cl] can be produced by reacting N-methyl chelidamic acid with thionyl chloride to produce 4,6-dichloro picolyl chloride, and then reacting the thus obtained 4,6-dichloro picolyl chloride with a lower alkanol (J. Org. Chem., 23, 1030(1958)).

Further, the above-mentioned compound (IX) ($T^1$=Cl and $Rn^1$=4-Cl) can also be produced by halogenating 4,6-dichloro picolinic acid obtained by oxidizing 4,6-dichloro2-methyl pyridine, using a halogenating agent such as thionyl chloride or phosphorus oxychloride to produce an acid halide, and then reacting the acid halide with a lower alkanol.

As oxidizing agents used for the above oxidation reaction, there may be exemplified chromic acid, permanganates such as potassium permanganate, ozone, halogens such as chlorine or bromine, hypo-halogen acid salts such as sodium hypobromite, lead dioxide, selenium dioxide-hydrogen peroxide, oxygen-oxidation in the presence of a base, nitric acid or the like.

These oxidizing agents can also be used in oxidation reactions described hereinafter.

By subjecting the thus obtained compound (IX) ($T^1$=Cl and $Rn^1$=4-Cl) as a raw material to nucleophilic substitution under a basic condition, 6-chloro-4-($C_1$ to $C_4$ alkoxy, $C_1$ to $C_4$ haloalkoxy, amino, $C_1$ to $C_4$ alkylamino or $C_1$ to $C_4$ alkylthio) picolinic acid lower-alkyl ester can be produced. In addition, by reacting the amino compound and the alkylamino compound with halogenated $C_1$ to $C_4$ alkyl and $C_7$ to $C_8$ aralkyl halide, respectively, under a basic condition, compounds having a di($C_1$ to $C_4$ alkyl)amino group or a $C_1$ to $C_4$ alkyl ($C_7$ to $C_8$ aralkyl) amino group bonded to the 4-position of the pyridine ring thereof, can be produced.

3,6-dichloro picolinic acid lower-alkyl ester [compound (IX): $T^1$=Cl and $Rn^1$=3-Cl] can be produced by esterifying a substituted picolinic acid (U.S. Pat. No. 3,317,549) obtained by hydrolyzing substituted 2-trihalomethyl pyridine which in turn is obtained by halogenating a 2-methyl group of 3,6-dichloro-2-methyl pyridine, with a lower alkanol. The above-mentioned process is accompanied with the halogenation reaction. Therefore, this process is preferably used in such a case where R is a halogen atom.

5-($C_1$ to $C_4$ alkoxy or $C_1$ to $C_4$ haloalkoxy)-6-halogeno-2-picolinic acid lower-alkyl ester [compound (IX): $T^1$=halogen atom and $Rn^1$=5-($C_1$ to $C_4$ alkoxy or $C_1$ to $C_4$ haloalkoxy)] can be produced by reacting a hydroxy group bonded to the 5-position of 6-halogeno-5-hydroxy-2-picoline with $C_1$ to $C_4$ alkyl or $C_1$ to $C_4$ haloalkoxy to convert the hydroxy group into an ether bond, thereby producing 5-($C_1$ to $C_4$ alkoxy or $C_1$ to $C_4$ haloalkoxy)-6-halogeno-2-picoline; oxidizing the 2-methyl group of the picoline into a carboxyl group to produce 5-($C_1$ to $C_4$ alkoxy or $C_1$ to $C_4$ haloalkoxy)6-halogeno-2-picolinic acid; and then esterifying the carboxyl group with a lower alkyl group.

Examples of the 6-bromo-5-methoxy compounds [compound (IX): $T^1$=Br and $Rn^1$=5-$OCH_3$] have been described in "Pharmazie 38(9), 591(1983)".

In the production of the substituted picolinic acid by oxidation reaction, in the case where any substituent is bonded to the 4-position of the pyridine ring, it is preferable to adopt a method of first producing 2-pyridine methanol from 2-picoline N-oxides and then oxidizing the hydroxymethyl group of the 2-pyridine methanol into a carboxyl group to produce the substituted picolinic acid, rather than such a method of directly oxidizing the 2-methyl group bonded to the pyridine ring into the carboxyl group. For example, 4-methoxy-6-chloro picolinic acid can be produced by oxidizing a hydroxymethyl group of 4-methoxy-6-chloro-2-pyridine methanol.

The compounds (I-c) involved in the above-mentioned present compound (I) and having at least one $C_1$ to $C_4$ alkylamino group in $R^2n^1$ thereof, can be produced by subjecting a phenylmethyl group of a $C_1$ to $C_4$ alkyl (phenylmethyl)amino group in $R^3n^1$ bonded to a corresponding position of the pyridine ring of the compound (I-d) which is also involved in the present compound (I), to hydrocracking or hydrogenolysis (hereinafter referred to merely as "step D").

The above reaction is represented by the following reaction formula:

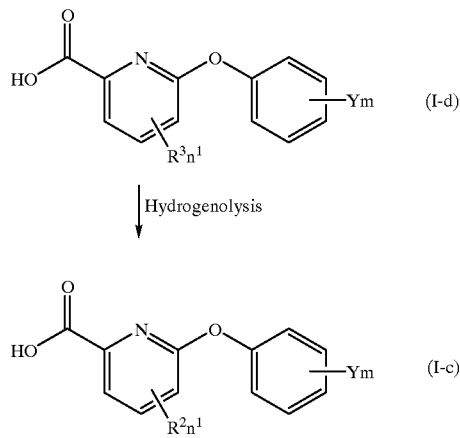

wherein Y, m and $n^1$ have the same definitions as described above; $R^2$ is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group or a di($C_1$ to $C_4$ alkyl)amino group, and at least one of $R^2n^1$ is necessarily a $C_1$ to $C_4$ alkylamino group; and $R^3$ is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl) amino group or a $C_7$ to $C_8$ aralkyl($C_1$ to $C_4$ alkyl)amino group, and at least one of $R^3n^1$ is necessarily a $C_1$ to $C_4$ alkyl(phenylmethyl)amino group.

As hydrogenation catalysts used for the above-mentioned hydrocracking or hydrogenolysis, there may be usually exemplified metals such as platinum, palladium, nickel or the like whose specific surface is increased in order to enhance a catalytic activity thereof, or these metals supported on activated carbon, carbon, barium carbonate, alumina or the like. Among these catalysts, palladium-carbon, Raney nickel, etc., are preferred. As reaction accelerators, among the above-mentioned acids, hydrochloric acid, perchloric acid, acetic acid or the like can be preferably used. The reaction may be conducted at a temperature of from room temperature to 100° C. for a period of from several minutes to several days, preferably from 30 minutes to 2 days.

The present compound (I) may be used as agricultural or horticultural fungicides as it is. However, the compound (I) may be usually formulated together with auxiliaries or adjuvants into various formulations such as dusting powder, water-dispersible powder, granules or emulsion. In this case, the obtained formulation may contain at least one compound (I) in an amount of usually 0.1 to 95% by weight, preferably 0.5 to 90% by weight, more preferably 2 to 70% by weight based on the weight of the formulation.

Examples of carriers or supports, diluents and surfactants used as the formulation auxiliaries or adjuvants are as follows. As solid carriers or supports, there may be usually exemplified talc, kaolin, bentonite, diatomite, white carbon, clay or the like. As liquid diluents, there may be usually exemplified water, xylene, toluene, chlorobenzene, cyclohexane, cyclohexanone, dimethyl sulfoxide, dimethyl formamide, alcohols or the like.

Various surfactants may be selectively used according to the effects thereof. As emulsions, there may be usually exemplified polyoxyethylene alkylaryl ether, polyoxyethylene sorbitan monolaurate or the like. As dispersants, there may be usually exemplified lignin sulfonate, dibutylnaphthalene sulfonate or the like. As wetting agents, there may be usually exemplified alkyl sulfonate, alkylphenyl sulfonate or the like.

The above-mentioned formulations are used as they are without diluting, or are used as formulations diluted with a diluent such as water to the predetermined concentration. In the case where the formulations are diluted upon use, the concentration of the present compound (I) in the formulations is usually in the range of 0.01 to 1.0%. The amount of the present compound (I) is usually 20 to 5,000 g, preferably 50 to 2,000 g per one hectare (ha) of agricultural or horticultural lands such as plowed field, paddy field, fruit farm, green house or the like. The concentrations and amounts of the formulations used may be varied according to types of formulations used, the time, method or place of use, kinds of crops to be treated or the like and, therefore, increased or reduced concentrations or amounts may also be used without being limited to the above-specified range. Further, the present compound (I) may be used in combination with other effective ingredients, for example, germicide, insecticide, miticide, herbicide or the like.

BEST MODE FOR CARRYING OUT THE INVENTION

The present invention will be described in more detail below by examples. However, these examples are not intended to limit the present invention, and various modifications and changes can be ordinarily made without departing from the scope of the present invention.

The compounds (I) used in these examples were produced by the following methods.

EXAMPLE 1

Production of 4-methoxy-6-[3-(trifluoromethyl) phenoxy] picolinic acid (Compound No. I-1)

(1) Production of 2-bromo-4-methoxy-6-[3-(trifluoromethyl)phenoxy] pyridine as an intermediate 3-(trifluoromethyl) phenol (3.34 g; 0.0187×1.1 mol) was dissolved in dimethyl formamide (hereinafter referred to merely as "DMF") (approximately 30 ml). Further, sodium hydride [0.78 g (ca. 60% in mineral oil), 0.0187×1.0 mol] and then 2,6-dibromo-4-methoxy pyridine (5.00 g, 0.0187 mol) were added to the solution. The obtained solution was stirred at about 120° C. for about 2 hours and, thereafter, allowed to stand so as to be cooled to room temperature. The obtained reaction solution was distributed in hexane-saturated sodium bicarbonate water. The organic phase separated from the reaction solution was washed with saturated brine, and dried with anhydrous sodium sulfate. The resultant solution was concentrated and then purified by silica gel column chromatography (eluting solution: ethyl acetate/hexane), and the obtained purified product was subjected to recrystallization using hexane, thereby obtaining an aimed product.

Yield weight: 3.23 g; yield by percentage: 50%; solid;
melting point: 57 to 60° C.;
$^1$H-NMR (60 MHz, CDCl$_3$, δ): 3.75(3H, s), 6.26(1H, d, J=2 Hz), 6.75(1H, d, J=2 Hz), 7.0–7.6(4H, complex).

(2) Production of 4-methoxy-6-[3-(trifluoromethyl) phenoxy] picolinic acid (compound No. I-1)

2-bromo-4-methoxy-6-[3-(trifluoromethyl)phenoxy] pyridine (3.00 g, 0.0086 mol) was suspended in about 30 ml of diethyl ether. While cooling in a dry ice-acetone bath in an argon atmosphere, the obtained suspension was mixed with n-butyl lithium [5.9 ml (ca. 1.6 M in hexane solution), 0.0086×1.1 mol], and the obtained mixture was stirred for about 10 minutes. After replacing an interior of the reactor with a carbon dioxide gas, the solution was removed from the bath and stirred at room temperature for about one hour. The obtained reaction solution was mixed with about 10 ml of a 1 N aqueous hydrochloric acid solution, distributed in ethyl acetate-water, and then washed with saturated brine. The organic phase separated from the solution was dried with anhydrous sodium sulfate, concentrated and then purified by silica gel column chromatography (eluting solution: ethyl acetate/hexane), thereby obtaining an aimed product.

Yield weight: 0.82 g; yield percentage: 30%; solid;
melting point: 85 to 88° C.;
$^1$ H-NMR (60 MHz, CDCl$_3$, δ): 3.84(3H, s), 6.55(1H, d, J=2 Hz), 7.0–7.6(5H, complex), 9.61(1H, s).

EXAMPLE 2

Production of 4-methoxy-6-[3-(trifluoromethyl) phenoxy] picolinic acid (Compound No. I-1)

(1) Production of 2-chloro-4-nitro pyridine N-oxide as an intermediate 2-chloro pyridine N-oxide hydrochloride (17.0 g, 0.102 mol) was mixed with sulfuric acid (64.0 g, 0.102×6.4 mol) and fuming nitric acid (36.0 g (ca. 94%), 0.102×5.3 mol), and the obtained mixture was stirred at a temperature of 90 to 100° C. for 2.5 hours. The obtained reaction mixture was added to 800 ml of ice water to form a precipitate. The precipitate was filtered out, washed with water and then dried. The water phase was extracted with ethyl acetate. The obtained extract was recrystallized with ethyl acetate and hexane.

Yield weight: 14.4 g; yield percentage: 81%; solid;
melting point: 151 to 153° C.;
$^1$H-NMR (60 MHz, CDCl$_3$, δ): 7.7–8.2(1H, mult.), 8.2–8.6(2H, complex).

(2) Production of 2-chloro-4-methoxy pyridine N-oxide as an intermediate 2-chloro-4-nitro pyridine N-oxide (13.4 g, 0.077 mol) was suspended in 100 ml of methanol. Sodium methoxide [14.8 g (ca. 28% in methanol solution), 0.077×1.0 mol] was dropped into the obtained suspension and dissolved therein at room temperature while stirring, and the suspension was further stirred for 2 days. The obtained reaction solution was distilled under reduced pressure to remove methanol therefrom. The distillation residue was dissolved in ethyl acetate. The obtained solution was filtered to remove sodium nitrite therefrom, and then ethyl acetate was distilled off, thereby obtaining an aimed product.

Yield weight: 12.1 g; yield percentage: 99%; solid;
decomposition point: about 90° C.;
$^1$H-NMR (60 MHz, CDCl$_3$, δ): 3.80(3H, s), 6.75(1H, d, J=3.5 Hz, 7.5 Hz), 6.99(1H, d, J=3.5 Hz), 8.21(1H, d, J=7.5 Hz).

(3) Production of 2-chloro-6-cyano-4-methoxy pyridine as an intermediate

Dimethyl sulfate (8.3 g, 0.070×1 mol) was dropped into 2-chloro-4-methoxy pyridine N-oxide (11.1 g, 0.070 mol). The obtained mixture was stirred at room temperature to obtain a homogeneous solution. Thereafter, the obtained homogeneous solution was further stirred overnight. The solution was washed with diethyl ether by decantation, and then dissolved in 70 ml of water. Sodium cyanide (8.3 g, 0.070×2.4 mol) dissolved in 70 ml of water was dropped into the obtained solution at −10° C. for about one hour in a nitrogen atmosphere. After stirring the reaction solution for 2 hours, the obtained precipitate was filtered out and washed with water. Thus water-washed precipitate was dissolved in ethyl acetate, added with hexane, treated with silica gel and then subjected to distillation to remove the solvent therefrom, thereby obtaining an aimed product.

Yield weight: 6.6 g; yield percentage: 56%; solid; melting point: 94 to 96° C.;
$^1$H-NMR (60 MHz, CDCl$_3$, δ): 3.86 (3H, s), 6.96 (1H, d, J=2 Hz), 7.11 (1H, d, J=2 Hz).

(4) Production of 2-cyano-4-methoxy-6-[3-(trifluoromethyl) phenoxy] pyridine as an intermediate 3-(trifluoromethyl) phenol (3.74 g, 0.0178×1.3 mol) was dissolved in about 20 ml of dimethyl formamide (hereinafter referred to as merely "DMF"). The obtained solution was further mixed with sodium hydride [0.81 g (ca. 60% in mineral oil), 0.0178×1.1 mol) and then with 2-chloro-6-cyano-4-methoxy pyridine (3.0 g, 0.0178 mol). The resultant solution was stirred at about 110° C. for about 5 hours. The obtained reaction solution was distributed in hexane-saturated sodium bicarbonate water and then washed with saturated brine. The organic phase separated from the reaction solution was dried with anhydrous sodium sulfate, concentrated and then purified by silica gel column chromatography (eluting solution: ethyl acetate/hexane), thereby obtaining an aimed product.

Yield weight: 3.74 g; yield percentage: 71%; solid; melting point: 88 to 90° C.;
$^1$H-NMR (60 MHz, CDCl$_3$, δ): 3.85 (3H, s), 6.54 (1H, d, J=2 Hz), 6.94 (1H, d, J=2 Hz), 6.9–7.6 (4H, complex).

(5) Production of 4-methoxy-6-[3-(trifluoromethyl) phenoxy] picolinic acid (compound No. I-1)

2-cyano-4-methoxy-6-[3-(trifluoromethyl)phenoxy] pyridine (1.0 g, 0.0034 mol) was suspended in about 10 ml of concentrated hydrochloric acid. The obtained suspension was stirred at about 100° C. for about 2 hours. After being allowed to stand for cooling, the obtained reaction solution was mixed with water, and then distributed in ethyl acetate-water. The organic phase of the solution was washed with saturated brine, dried with anhydrous sodium sulfate, concentrated and then purified by silica gel column chromatography (eluting solution: ethyl acetate/hexane), thereby obtaining an aimed product.

Yield weight: 0.92 g; yield percentage: 86%.

EXAMPLE 3

Production of 4-methoxy-6-[3-(trifluoromethoxy) phenoxy] picolinic acid (Compound No. I-2)

(1) Production of 2-cyano-4-methoxy-6-[3-(trifluoromethoxy) phenoxy] pyridine as an intermediate 3-(trifluoromethoxy) phenol (1.7 g, 0.0089×1.1 mol) was dissolved in about 20 ml of DMF. The obtained solution was further mixed with sodium hydride [0.39 g (ca. 60% in mineral oil), 0.0089×1.1 mol) and then with 2-chloro-6-cyano-4-methoxy pyridine (1.5 g, 0.0089 mol). The resultant mixture was stirred at about 110° C. for about 4 hours. The obtained reaction solution was distributed in ethyl acetate-saturated sodium bicarbonate water and then washed with saturated brine. The organic phase separated from the solution was dried with anhydrous sodium sulfate, concentrated and then purified by silica gel column chromatography (eluting solution: ethyl acetate/hexane), thereby obtaining an aimed product.

Yield weight: 1.82 g; yield percentage: 66%; solid; melting point: 64 to 66° C.;
$^1$H-NMR (60 MHz, CDCl$_3$, δ): 3.81 (3H, s), 6.52 (1H, d, J=2 Hz), 6.7–7.6 (5H, complex).

(2) Production of 4-methoxy-6-[3-(trifluoromethoxy) phenoxy] picolinic acid (compound No. I-2)

2-cyano-4-methoxy-6-[3-(trifluoromethoxy)phenoxy] pyridine (1.72 g, 0.0055 mol) was suspended in about 15 ml of concentrated hydrochloric acid. The obtained suspension was stirred at about 100° C. for about 4 hours. After being allowed to stand for cooling, the obtained reaction solution was mixed with water, and then distributed in ethyl acetate-water. The organic phase separated from the solution was washed with saturated brine, dried with anhydrous sodium sulfate and then concentrated, thereby obtaining an aimed product.

Yield weight: 1.80 g; yield percentage: 99%; solid; melting point: 70 to 71° C.;
$^1$H-NMR (60 MHz, CDCl$_3$, δ): 3.88 (3H, s), 6.57 (1H, d, J=2 Hz), 6.7–7.7 (4H, complex), 7.44 (1H, d, J=2 Hz), 9.09 (1H, s).

EXAMPLE 4

Production of 4-methyl-6-[3-(trifluoromethyl) phenoxy] picolinic acid (Compound No. I-5)

(1) Production of 2-chloro-4-methyl pyridine as an intermediate 2-hydroxy-4-methyl pyridine (20.3 g, 0.186 mol) was heated and stirred in 50 ml of phosphorus oxychloride at 100° C. for 4 hours. The obtained reaction solution was poured into ice water, and then sodium carbonate was added thereto to form an alkalescent solution. The obtained alkalescent solution was extracted with 200 ml of chloroform two times. The obtained extract solution was washed with saturated brine, dried with anhydrous sodium sulfate, and then subjected to distillation under reduced pressure to remove the solvent therefrom. The distillation residues were purified by silica gel column chromatography (eluting solution: ethyl acetate/hexane), thereby obtaining an aimed product.

Yield weight: 23 g; yield percentage: 97%; oily substance;
$^1$H-NMR (60 MHz, CDCl$_3$, δ): 2.26(3H, s), 6.8–7.1 (2H, complex), 8.1 (1H, d, J=4 Hz).

(2) Production of 2-chloro-4-methyl pyridine N-oxide as an intermediate 2-chloro-4-methyl pyridine (24.0 g, 0.188 mol) was dissolved in 240 ml of acetic acid. The obtained solution was mixed with a 31% aqueous hydrogen peroxide solution (203.9 g, 0.188×9.9 mol), and then stirred at 65° C. for 18 hours. Thereafter, the obtained reaction solution was poured into ice water, and then sodium carbonate was added thereto to form an alkalescent solution. The obtained alkalescent solution was extracted with 300 ml of chloroform two times. The obtained extract solution was washed with 100 ml of a saturated aqueous sodium sulfite solution and further with saturated brine, and then distilled to remove the solvent therefrom, thereby obtaining an aimed product including the raw material.

Rough Yield weight: 36 g; rough yield percentage: 96%.

(3) Production of 6-chloro-2-cyano-4-methyl pyridine as an intermediate 2-chloro-4-methyl pyridine N-oxide (12 g, 0.0836 mol) was gradually added into dimethyl sulfate (12.5 g, 0.0836× 1.2 mol). The obtained solution was stirred overnight. Thereafter, the obtained reaction mixture was mixed with 40 ml of ether and then stirred. Successively, the ether was removed from the reaction mixture by decantation, and further the residual ether was distilled off from the reaction mixture under reduced pressure. The distillation residues were dissolved in 40 ml of water (solution A). Separately, sodium cyanide (16 g, 0.0836 mol×3.9 mol) was dissolved in 78 ml of water, and cooled to a temperature of –7° C. to –15° C. in a nitrogen atmosphere. The above-prepared solution A was dropped into the sodium cyanide solution. The obtained solution was stirred at the above temperature for 1.5 hours, thereby precipitating crystals. The precipitated crystals was filtered out and washed with water. The obtained solid was further washed with a small amount of acetic acid, thereby obtaining an aimed product.

Yield weight: 6.88 g; yield percentage: 54%; solid; melting point: 96 to 97° C.;
$^1$H-NMR (60 MHz, CDCl$_3$, δ): 2.4 (3H, s), 7.3 (1H, s), 7.4 (1H, s).

(4) Production of 2-cyano-4-methyl-6-[3-(trifluoromethyl) phenoxy] pyridine as an intermediate 3-(trifluoromethyl) phenol (1.75 g, 0.0098×1.1 mol) was dissolved in 5 ml of dried dioxane. Sodium hydride (0.413 g (ca. 60% in mineral oil), 0.0098×1.05 mol) was added to the obtained solution. After completion of the foaming, a solution obtained by dissolving 6-chloro-2-cyano4-methyl pyridine (1.5 g, 0.0098 mol) in 5 ml of dried dioxane, and copper iodide (0.18 g, 0.0098×0.1 mol) were added to the above solution, and then the obtained mixture was heated and stirred in an oil bath maintained at 110° C., for 5 hours. Thereafter, the obtained reaction solution was distilled under reduced pressure. The obtained distillation residues were mixed with 15 ml of water, and filtered through a glass filter provided with High-Flow Super Cell. The obtained filter cake was washed with ethyl acetate, and further a filtrate obtained therefrom was extracted with ethyl acetate. The resultant extract solution was subjected to distillation under reduced pressure to remove the solvent therefrom, thereby obtaining an aimed product.

Yield weight: 2.23 g; yield percentage: 82%; oily substance;
$^1$H-NMR (60 MHz, CDCl$_3$, δ): 2.4 (3H, s), 6.8–7.5 (6H, complex).

(5) Production of 4-methyl-6-[3-(trifluoromethyl)phenoxy] picolinic acid (Compound No. I-5)

2-cyano-4-methyl-6-[3-(trifluoromethyl)phenoxy] pyridine (2.055 g, 0.0074 mol) was heated and stirred in 10 ml of concentrated hydrochloric acid and 6 ml of acetic acid at 100° C. for 5 hours. Thereafter, the obtained reaction solution was concentrated under reduced pressure. The obtained residues were mixed with water. The precipitated solids were filtered out, washed with water, and then dried.

Yield weight: 1.49 g; yield percentage: 68%; solid; melting point: 75 to 77° C.;
$^1$H-NMR (60 MHz, CDCl$_3$, δ): 2.4 (3H, s), 6.8–7.8 (6H, complex), 9.6 (1H, brs).

EXAMPLE 5

Production of 4-chloro-6-[3-(trifluoromethyl) phenoxy] picolinic acid (Compound No. I-6)

(1) Production of 4-chloro-6-[3-(trifluoromethyl)phenoxy] picolinic acid methyl ester as an intermediate 3-(trifluoromethyl) phenol (3.15 g, 0.0019 mol) was dissolved in 50 ml of dried dioxane. Sodium hydride (0.8 g (ca. 60% in mineral oil), 0.0019×1.05 mol) was added to the obtained solution at room temperature. After completion of the foaming, a solution obtained by dissolving 4,6-dichloro picolinic acid methyl ester (4.0 g, 0.0019 mol) in 5 ml of dried dioxane, was dropped into the above solution. Successively, copper iodide (3.7 g, 0.0019×1.0 mol) was added to the obtained solution. The resultant mixture was heated and stirred at a temperature of 120 to 130° C. for 10 hours. Thereafter, the obtained reaction solution was cooled, mixed with 10 ml of water, and then filtered through a glass filter provided with High-flow Super Cell. The obtained filtrate was extracted with 100 ml of ethyl acetate two times, thereby separating an organic phase therefrom. The obtained organic phase was dried with sodium anhydride. After the dried organic phase was subjected to distillation to remove the solvent therefrom, the obtained distillation residues were purified by silica gel column chromatography (eluting solution: ethyl acetate/hexane), thereby obtaining an aimed product.

Yield weight: 3.14 g; yield percentage: 49%; solid; melting point: 81 to 82° C.;
$^1$H-NMR (60 MHz, CDCl$_3$, δ): 3.83 (3H, s), 7.00 (1H, d, J=2 Hz), 7.2–7.6 (4H, complex), 7.75 (1H, d, J=2 Hz).

(2) Production of 4-chloro-6-[3-(trifluoromethyl)phenoxy] picolinic acid (Compound No. I-6)

4-chloro-6-[3-(trifluoromethyl)phenoxy] picolinic acid methyl ester (3.1 g, 0.0093 mol) was dissolved in 40 ml of ethanol. 4 ml of an aqueous solution of sodium hydroxide (0.41 g, 0.0093×1.1 mol) was added to the obtained solution. The resultant mixture was heated and stirred at 60° C. for 20 minutes. Thereafter, the obtained reaction solution was cooled and distilled under reduced pressure to remove ethanol therefrom. The obtained residual solution was treated with concentrated hydrochloric acid so as to adjust the pH thereof to 3. The precipitated solids were filtered out from the above residual solution, washed with water and then dried, thereby obtaining an aimed product.

Yield weight: 2.57 g; yield percentage: 87%; solid; melting point: 119 to 120° C.;
$^1$H-NMR (60 MHz, DMSO-d$_6$, δ): 4.3–4.9 (1H, br), 7.28 (1H, d, J=2 Hz), 7.5–7.3 (4H, complex), 7.63 (1H, d, J=2 Hz).

EXAMPLE 6

Production of 4-dimethylamino-6-[3-(trifluoromethyl)phenoxy] picolinic acid (Compound No. I-7)

(1) Production of 2-bromo-4-dimethylamino-6-[3-(trifluoromethyl)phenoxy] pyridine as an intermediate 3-(trifluoromethyl) phenol (1.4 g, 0.0071×1.2 mol) was dissolved in DMF (about 20 ml). Further, sodium hydride (0.30 g (ca. 60% in mineral oil), 0.0071×1.06 mol) and then 2,6-dibromo-4-dimethylamino pyridine (2.00 g, 0.0071 mol) were added to the obtained solution. The resultant solution was refluxed for about 6 hours, and thereafter allowed to stand for cooling to room temperature. The obtained reaction solution was distributed in hexane-saturated sodium bicarbonate water. The organic phase separated from the solution was washed with saturated brine, dried with anhydrous sodium sulfate, concentrated and purified by silica gel column chromatography (eluting solution: ethyl acetate/hexane). The purified product was subjected recrystallization using hexane, thereby obtaining an aimed product.

Yield weight: 1.67 g; yield percentage: 65%; solid; melting point: 61 to 66° C.;
$^1$H-NMR (60 MHz, CDCl$_3$, δ): 2.86 (6H, s), 6.88 (1H, d, J=2 Hz), 6.38 (1H, d, J=2 Hz), 6.9–7.5 (4H, complex).

(2) Production of 4-dimethylamino-6-[3-(trifluoromethyl) phenoxy] picolinic acid (compound No. I-7)

2-bromo-4-dimethylamino-6-[3-(trifluoromethyl) phenoxy] pyridine (5.00 g, 0.0138 mol) was dissolved in about 200 ml of diethyl ether. While cooling in a dry ice-acetone bath in an argon atmosphere, the obtained solution was mixed with n-butyl lithium [9.2 ml (ca. 1.66 M in hexane solution), 0.0138×1.1 mol], and then stirred for about 10 minutes. After the interior of the reactor was replaced with a carbon dioxide gas, the solution was removed from the bath and stirred at room temperature for about one hour. The reaction solution was mixed with about 15 ml of a 4 N aqueous hydrochloric acid solution, distributed in ethyl acetate-water, and then washed with saturated brine. The organic phase separated from the solution was dried with anhydrous sodium sulfate, concentrated and then purified by silica gel column chromatography (eluting solution: ethyl acetate/hexane), thereby obtaining an aimed product.

Yield weight: 2.36 g; yield percentage: 52%; solid; melting point: 141 to 143° C.;

$^1$H-NMR (60 MHz, CDCl$_3$, δ): 3.04(6H, s), 6.17(1H, d, J=2 Hz), 6.8–7.8(4H, complex), 7.21(1H, d, J=2 Hz), 10.02 (1H, s).

EXAMPLE 7

Production of 4-methylmercapto-6-[3-(trifluoromethyl) phenoxy] picolinic acid (Compound No. I-8)

(1) Production of 2-bromo-4-methylmercapto-6-[3-(trifluoromethyl)phenoxy] pyridine as an intermediate 3-(trifluoromethyl) phenol (2.06 g, 0.0106×1.2 mol) was dissolved in DMF (about 20 ml). Further, sodium hydride (0.45 g (ca. 60% in mineral oil), 0.0106×1.06 mol) and then 2,6-dibromo-4-methylmercapto pyridine (3.00 g, 0.0106 mol) were added to the obtained solution. The solution was stirred at 100° C. for about 2 hours, and then allowed to stand for cooling to room temperature. The obtained reaction solution was distributed in hexane-saturated sodium bicarbonate water. The organic phase separated from the solution was washed with saturated brine, and dried with anhydrous sodium sulfate. The obtained solution was concentrated and then purified by silica gel column chromatography (eluting solution: ethyl acetate/hexane). The purified product was subjected recrystallization using hexane, thereby obtaining an aimed product.

Yield weight: 2.49 g; yield percentage: 64%; solid; melting point: 54 to 57° C.;

$^1$H-NMR (60 MHz, CDCl$_3$, δ): 2.37(3H, s), 6.50(1H, d, J=2 Hz), 6.89(1H, d, J=2 Hz), 7.0–7.5(4H, complex).

(2) Production of 4-methylmercapto-6-[3-(trifluoromethyl) phenoxy] picolinic acid (compound No. I-8)

2-bromo-4-methylmercapto-6-[3-(trifluoromethyl) phenoxy] pyridine (5.00 g, 0.0137 mol) was dissolved in about 200 ml of diethyl ether. While cooling in a dry ice-acetone bath in an argon atmosphere, the obtained solution was mixed with n-butyl lithium [9.3 ml (ca. 1.63 M in hexane solution), 0.0137×1.1 mol] and then stirred for about 10 minutes. After the interior of the reactor was replaced with a carbon dioxide gas, the solution was removed from the bath and stirred at room temperature for about one hour. The obtained reaction solution was mixed with about 15 ml of a 4 N aqueous hydrochloric acid solution. The obtained solution was distributed in ethyl acetate-water and then washed with saturated brine. The organic phase separated from the solution was dried with anhydrous sodium sulfate, concentrated and then purified by silica gel column chromatography (eluting solution: ethyl acetate/hexane), thereby obtaining an aimed product.

Yield weight: 2.22 g; yield percentage: 49%; solid; melting point: 96 to 99° C.;

$^1$H-NMR (60 MHz, CDCl$_3$, δ): 2.50(3H, s), 6.88(1H, d, J=2 Hz), 7.0–7.7(4H, complex), 7.66(1H, d, J=2 Hz), 9.40 (1H, s).

EXAMPLE 8

Production of 4-[methyl(phenylmethyl)amino]-6-[3-(trifluoromethyl)phenoxy] picolinic acid (Compound No. I-9)

(1) Production of 2-bromo-4-[methyl(phenylmethyl) amino]-6-[3-(trifluoromethyl)phenoxy] pyridine as an intermediate 3-(trifluoromethyl) phenol (1.56 g, 0.0080×1.2 mol) was dissolved in DMF (about 20 ml). Further, sodium hydride (0.34 g (ca. 60% in mineral oil), 0.0080×1.06 mol) and then 4-[methyl(phenylmethyl)amino]-2,6-dibromo pyridine (2.85 g, 0.0080 mol) were added to the obtained solution. The resultant solution was refluxed for about 6 hours, and then allowed to stand for cooling to room temperature. The obtained reaction solution was distributed in hexane-saturated sodium bicarbonate water. The organic phase separated from the solution was washed with saturated brine, and then dried with anhydrous sodium sulfate. The obtained solution was concentrated and then purified by silica gel column chromatography (eluting solution: ethyl acetate/hexane). The purified product was subjected recrystallization using hexane, thereby obtaining an aimed product.

Yield weight: 2.15 g; yield percentage: 61%; solid; melting point: 84 to 87° C.;

$^1$H-NMR (60 MHz, CDCl$_3$, δ): 2.92(3H, s), 4.83(2H, s), 5.95(1H, d, J=2 Hz), 6.48(1H, d, J=2 Hz), 6.7–7.6(9H, complex).

(2) Production of 4-[methyl(phenylmethyl)amino]-6-[3-(trifluoromethyl)phenoxy] picolinic acid (compound No. I-9)

2-bromo-4-[methyl(phenylmethyl)amino]-6-[3-(trifluoromethyl)phenoxy] pyridine (6.38 g, 0.0146 mol) was dissolved in about 300 ml of diethyl ether. While cooling in a dry ice-acetone bath in an argon atmosphere, the obtained solution was mixed with n-butyl lithium [10 ml (ca. 1.63 M in hexane solution), 0.0146×1.1 mol] and then stirred for about 10 minutes. After the interior of the reactor was replaced with a carbon dioxide gas, the solution was removed from the bath and stirred at room temperature for about one hour. The obtained reaction solution was mixed with about 30 ml of a 1 N aqueous hydrochloric acid solution, distributed in ethyl acetate-water, and then washed with saturated brine. The organic phase separated from the solution was dried with anhydrous sodium sulfate, concentrated, and then purified by silica gel column chromatography (eluting solution: ethyl acetate/hexane), thereby obtaining an aimed product.

Yield weight: 3.09 g; yield percentage: 53%; solid; melting point: 80 to 82° C.;

$^1$H-NMR (60 MHz, CDCl$_3$, δ): 3.05(3H, s), 4.52(2H, s), 6.18(1H, d, J=2 Hz), 6.7–7.6(10H, complex), 9.83(1H, s).

EXAMPLE 9

Production of 4-methylamino-6-[3-(trifluoromethyl) phenoxy] picolinic acid (Compound No. I-10)

4-[methyl(phenylmethyl)amino]-6-[3-(trifluoromethyl) phenoxy] picolinic acid (0.42 g, 0.0010 mol) and a small amount of 10% palladium/carbon were added to about 30 ml of methanol. The obtained mixture was stirred at room temperature for about 10 hours in a hydrogen atmosphere. The obtained reaction solution was filtered using High-Flow Super Cell, and then concentrated, thereby obtaining an aimed product.

Yield weight: 0.34 g; yield percentage: 100%; solid; melting point: 66 to 68° C.;

$^1$H-NMR (60 MHz, CDCl$_3$, δ): 2.90(3H, s), 5.3(1H, brs), 6.11(1H, s), 6.7(1H, brs), 7.0–8.0(5H, complex).

EXAMPLE 10

Production of 3-chloro-6-[3-(trifluoromethyl) phenoxy] picolinic acid (Compound No. I-11)

(1) Production of 2,5-dichloro pyridine N-oxide as an intermediate 2,5-dichloro pyridine (20 g, 0.135 mol) was dissolved in 240 ml of acetic acid. The obtained solution was mixed with a 31% aqueous hydrogen peroxide solution (92.5 g, 0.135× 6.24 mol), and then stirred at 65° C. for 18 hours. Thereafter, the obtained reaction solution was poured into ice water, and then sodium carbonate was added thereto to form an alkalescent solution. The obtained alkalescent solution was extracted with 200 ml of chloroform two times. The obtained extract solution was washed with 50 ml of a saturated aqueous sodium sulfite solution and then with saturated brine. The obtained solution was distilled to remove the solvent therefrom, thereby obtaining a white solid.

Yield weight: 11.9 g; yield percentage: 54%; solid; melting point: 77 to 80° C.;
$^1$H-NMR (60 MHz, CDCl$_3$, δ): 7.15(1H, dd, J=2 Hz, 8 Hz), 7.4(1H, d, J=8 Hz), 8.3(1H, d, J=2 Hz).

(2) Production of 3,6-dichloro-2-cyano pyridine as an intermediate 2,5-dichloro pyridine N-oxide (11.7 g, 0.071 mol) was gradually added into dimethyl sulfate (9 g, 0.071×1.0 mol). The obtained mixture was stirred overnight. Thereafter, the obtained reaction mixture was mixed with 50 ml of ether, and stirred. Then, the ether was removed from the reaction mixture by decantation, and the residual ether was distilled off from the reaction mixture under reduced pressure. The distillation residues were dissolved in 50 ml of water (solution A). Separately, sodium cyanide (13.77 g, 0.071× 4.0 mol) was dissolved in 67 ml of water, and cooled to a temperature of –7° C. to –15° C. in a nitrogen atmosphere. The above-prepared solution A was dropped into the sodium cyanide solution. The obtained solution was stirred at the above temperature for 1.5 hours, thereby precipitating crystals. The precipitated crystals was filtered out and washed with water. The obtained solid was washed with a small amount of acetic acid, thereby obtaining an aimed product.

Yield weight: 6.6 g; yield percentage: 54%; solid; melting point: 90 to 92° C.;
$^1$H-NMR (60 MHz, CDCl$_3$, δ): 7.4(1H, d, J=8 Hz), 7.8(1H, d, J=8 Hz).

(3) Production of 3-chloro-2-cyano-6-[3-(trifluoromethyl) phenoxy] pyridine as an intermediate 3-(trifluoromethyl) phenol (3.09 g, 0.0173×1.1 mol) was dissolved in 10 ml of dried dioxane. Sodium hydride (0.728 g (ca. 60% in mineral oil), 0.00173×1.05 mol) was added to the obtained solution. After completion of the foaming, a solution obtained by dissolving 3,6-dichloro-2-cyano pyridine (3 g, 0.0173 mol) in 10 ml of dried dioxane, and copper iodide (0.33 g, 0.0173×0.1 mol) were added to the solution, and then the obtained mixture was heated and stirred in an oil bath maintained at 110° C., for 5 hours. Thereafter, the obtained reaction solution was distilled under reduced pressure. The obtained distillation residues were mixed with 30 ml of water, and filtered through a glass filter provided with High-flow Super Cell. The obtained filter cake was washed with ethyl acetate, and further a filtrate obtained therefrom was extracted with ethyl acetate. The resultant extract solution was distilled under reduced pressure to remove the solvent therefrom, thereby obtaining a solid product.

Yield weight: 4.26 g; yield percentage: 82%; solid; melting point: 63 to 65° C.;
$^1$H-NMR (60 MHz, CDCl$_3$, δ): 7.1(1H, d, J=8 Hz), 7.1–7.6(4H, complex), 7.8(1H, d, J=8 Hz).

(4) Production of 3-chloro-6-[3-(trifluoromethyl)phenoxy] picolinic acid (compound No. I-11)

3-chloro-2-cyano-6-[3-(trifluoromethyl)phenoxy] pyridine (2.58 g, 0.086 mol) was dissolved in 30 ml of 90% sulfuric acid. The obtained solution was heated and stirred at 120° C. for 1.5 hours. Thereafter, the obtained reaction solution was poured into ice water, and then mixed with sodium carbonate to form a weak-acidic solution, thereby precipitating solids. The precipitated solids were filtered out, washed with water, and then dried.

Yield weight: 1.68 g; yield percentage: 61%; solid; melting point: 80 to 83° C.;
$^1$H-NMR (60 MHz, CDCl$_3$, δ): 7.1(1H, d, J=9 Hz), 7.2–7.5(4H, complex), 7.8(1H, d, J=9 Hz), 9.6(1H, br).

EXAMPLE 11

Production of 5-methoxy-6-[3-(trifluoromethyl) phenoxy] picolinic acid (Compound No. I-12)

(1) Production of 5-methoxy-6-[3-(trifluoromethyl) phenoxy] picolinic acid methyl ester as an intermediate 3-(trifluoromethyl) phenol (1.317 g, 0.0081 mol) was dissolved in 10 ml of dried dimethyl acetamide. While cooling the obtained solution with water, sodium hydride (0.39 g (ca. 60% in mineral oil), 0.0081×1.2 mol) was added to the solution. After completion of the foaming, a solution obtained by dissolving 6-bromo-5-methoxy-2-pyridine carboxylic acid methyl ester (2.0 g, 0.0081 mol) in 10 ml of dried dimethyl acetamide, and then copper iodide (1.55 g, 0.081 mol) were successively added to the solution. The obtained mixture was heated and stirred at 120° C. for 10 hours. Thereafter, the obtained reaction solution was cooled, mixed with 50 ml of water and then with 50 ml of ethyl acetate, and filtered through a glass filter provided with High-flow Super Cell. The obtained filtrate was extracted with ethyl acetate to obtain an aimed product. An organic phase was separated from the product, washed with water, and then dried with anhydrous sodium sulfate. The dried product was concentrated, and the obtained residues were purified by silica gel column chromatography (eluting solution: ethyl acetate/hexane).

Yield weight: 0.68 g; yield percentage: 26%; solid; melting point: 116 to 118° C.;
$^1$H-NMR (60 MHz, CDCl$_3$, δ): 3.76(3H, s), 3.86(3H, s), 7.16(1H, d, J=8 Hz), 7.2–7.5(4H, complex), 7.80(1H, d, J=8 Hz).

(2) Production of 5-methoxy-6-[3-(trifluoromethyl) phenoxy] picolinic acid (compound No. I-12)

5-methoxy-6-[3-(trifluoromethyl)phenoxy] picolinic acid methyl ester (0.7 g, 0.0021 mol) was dissolved in 2.8 ml of ethyl alcohol. One milliliter of an aqueous solution of sodium hydroxide (0.102 g, 0.0021×1.2 mol) was added to the obtained solution. The resultant mixture was heated and stirred at 70° C. for 1.5 hours. After cooling, the obtained reaction solution was mixed with 2 ml of concentrated hydrochloric acid, thereby precipitating solids. The precipitated solids were filtered out from the solution, washed with water, and then dried.

Yield weight: 0.63 g; yield percentage: 94%; solid; melting point: 145 to 147° C.;
$^1$H-NMR (60 MHz, DMSO-d$_6$, δ): 3.80(3H, s), 7.1–7.6 (4H, complex), 7.46(1H, d, J=8 Hz), 7.76(1H, d, J=8 Hz), COOH was unclear.

EXAMPLE 12

Production of 6-[3-(trifluoromethyl)phenoxy)] picolinic acid (Compound No. I-13)

(1) Production of 2-cyano-6-[3-(trifluoromethyl)phenoxy] pyridine as an intermediate 3-(trifluoromethyl) phenol (4.21 g, 0.0217×1.2 mol) was dissolved in DMF (about 30 ml). Further, sodium hydride (0.95 g (ca. 60% in mineral oil), 0.0217×1.1 mol) and then 2-chloro-6-cyano pyridine (3.00 g, 0.0217 mol) were successively added to the obtained solution. The resultant solution was stirred at about 120° C. for about 4 hours, and then allowed to stand for cooling to room temperature. The obtained reaction solution was distributed in hexane-saturated sodium bicarbonate water. The organic phase separated from the solution was washed with saturated brine, and then dried with anhydrous sodium sulfate. The obtained solution was concentrated and then purified by silica gel column chromatography (eluting solution: ethyl acetate/hexane). The purified product was distilled to remove 3-(trifluoromethyl) phenol contained therein, and then subjected to recrystallization using hexane, thereby obtaining an aimed product.

Yield weight: 4.34 g; yield percentage: 76%; solid; melting point: 47 to 49° C.;

$^1$H-NMR (60 MHz, CDCl$_3$, δ): 7.08(1H, d, J=8 Hz), 6.6–7.7(5H, complex), 8.71(1H, t, J=8 Hz).

(2) Production of 6-[3-(trifluoromethyl)phenoxy] picolinic acid (compound No. I-13)

2-cyano-6-[3-(trifluoromethyl)phenoxy] pyridine (3.00 g, 0.011 mol) was suspended in about 15 ml of concentrated hydrochloric acid. The obtained suspension was stirred at about 100° C. for about 2 hours. After being allowed to stand for cooling, the obtained reaction solution was mixed with water, and then distributed in ethyl acetate-water. The organic phase separated from the solution was washed with saturated brine, dried with anhydrous sodium sulfate, concentrated and then purified by silica gel column chromatography (eluting solution: ethyl acetate/hexane), thereby obtaining an aimed product.

Yield weight: 3.02 g; yield percentage: 94%; solid; melting point: 88 to 90° C.;

$^1$H-NMR (60 MHz, CDCl$_3$, δ): 6.8–7.6(5H, complex), 7.6–8.2 (2H, complex), 10.17(1H, s).

EXAMPLE 13

Production of 4-(2,2,2-trifluoroethoxy)-6-[3-(trifluoromethyl)phenoxy] picolinic acid (Compound No. I-22)

(1) Production of 2-bromo-4-(2,2,2-trifluoroethoxy)-6-[3-(trifluoromethyl)phenoxy] pyridine as an intermediate 2,6-dibromo-4-(2,2,2-trifluoroethoxy) pyridine (13.0 g, 0.039 mol) and 3-(trifluoromethyl) phenol (7.55 g, 0.039× 1.2 mol) was dissolved in DMF (about 150 ml). Further, sodium hydride (1.7 g (ca. 60% in mineral oil), 0.039×1.1 mol) was added to the obtained solution. The resultant mixture was stirred at about 110° C. for about 4 hours, and then allowed to stand for cooling to room temperature. The obtained reaction solution was distributed in hexane-saturated sodium bicarbonate water. The organic phase separated from the solution was washed with saturated brine, and dried with anhydrous sodium sulfate. The obtained solution was concentrated and then purified by silica gel column chromatography (eluting solution: ethyl acetate/hexane). The purified product was subjected to recrystallization using hexane, thereby obtaining an aimed product.

Yield weight: 9.81 g; yield percentage: 61%; oily substance;

$^1$H-NMR (60 MHz, CDCl$_3$, δ): 4.28(2H, q, J=8 Hz), 6.29(1H, d, J=2 Hz), 6.76(1H, d, J=2 Hz), 7.0–7.6(4H, complex).

(2) Production of 4-(2,2,2-trifluoroethoxy)-6-[3-(trifluoromethyl)phenoxy] picolinic acid (compound No. I-22)

2-bromo-4-(2,2,2-trifluoroethoxy)-6-[3-(trifluoromethyl)phenoxy] pyridine (9.81 g, 0.0236 mol) was dissolved in about 200 ml of diethyl ether. While cooling in a dry ice-acetone bath in an argon atmosphere, the obtained solution was mixed with n-butyl lithium [16 ml (ca. 1.63 M in hexane solution), 0.0236×1.1 mol]. The obtained mixture was stirred for about 10 minutes. After replacing an interior of the reactor with a carbon dioxide gas, the solution was removed from the bath and stirred at room temperature for about one hour. The obtained reaction solution was mixed with about 15 ml of a 4 N aqueous hydrochloric acid solution, and then distributed in ethyl acetate-water. The organic phase separated from the solution was washed with saturated brine, dried with anhydrous sodium sulfate, concentrated and then purified by silica gel column chromatography (eluting solution: ethyl acetate/hexane). The purified product was recrystallized by adding hexane thereto, thereby obtaining an aimed product.

Yield weight: 3.26 g; yield percentage: 36%; solid; melting point: 93 to 95° C.;

$^1$H-NMR (60 MHz, CDCl$_3$, δ): 4.44(2H, q, J=8 Hz), 6.68(1H, d, J=2 Hz), 6.9–7.8(5H, complex), 9.23(1H, s).

EXAMPLE 14

Production of 4-methoxy-6-[2-chloro-6-(trifluoromethyl) phenoxy] picolinic acid (Compound No. I-33)

(1) Production of 2-cyano-4-methoxy-6-[2-chloro-6-(trifluoromethyl)phenoxy] pyridine as an intermediate 2-chloro-6-(trifluoromethyl) phenol (4.2 g, 0.0178×1.2 mol) was dissolved in about 20 ml of dimethyl formamide. Further, sodium hydride (0.82 g (ca. 60% in mineral oil), 0.0178×1.15 mol) and then 2-chloro-6-cyano-4-methoxy pyridine (3.0 g, 0.0178 mol) were successively added to the obtained solution. The resultant mixture was stirred at about 110° C. for about 5 hours. The obtained reaction solution was distributed in hexane-saturated sodium bicarbonate water, and washed with saturated brine. The organic phase separated from the solution was dried with anhydrous sodium sulfate, concentrated and then purified by silica gel column chromatography (eluting solution: ethyl acetate/ hexane), thereby obtaining an aimed product.

Yield weight: 2.98 g; yield percentage: 51%; solid; melting point: 110 to 112° C.;

$^1$H-NMR (60 MHz, CDCl$_3$, δ): 3.83(3H, s), 6.54(1H, d, J=2 Hz), 6.93(1H, d, J=2 Hz), 7.0–7.6(3H, complex).

(2) Production of 4-methoxy-6-[2-chloro-6-(trifluoromethyl) phenoxy] picolinic acid (compound No. I-33)

2-cyano-4-methoxy-6-[2-chloro-6-(trifluoromethyl) phenoxy] pyridine (2.88 g, 0.0088 mol) was suspended in about 20 ml of concentrated hydrochloric acid and about 10 ml of acetic acid. The obtained suspension was stirred at about 100° C. for about 4 hours. After being allowed to stand for cooling, the obtained reaction solution was mixed with water, and then distributed in chloroform-water. The obtained solution was washed with saturated brine, dried with anhydrous sodium sulfate and then concentrated, thereby obtaining an aimed product.

Yield weight: 2.73 g; yield percentage: 90%; solid; melting point: 125 to 127° C.;

$^1$H-NMR (60 MHz, CDCl$_3$, δ): 3.90(3H, s), 6.59(1H, d, J=2 Hz), 6.9–7.7(4H, complex), 9.06(1H, s).

Compounds shown in the following Tables 4 to 7 were produced according to methods as described in the above Production Examples 1 to 14. The properties and NMR data of these compounds are also shown in Tables 4 to 7 below.

TABLE 4

| Compound No.[c] | Properties | NMR[d] 60MHz, δ |
|---|---|---|
| I-1<br>A, B | Solid;<br>m.p.: 85–88° C. | 3.84(3H, s),<br>6.55(1H, d, J=2Hz),<br>7.0–7.6(5H, complex),<br>9.61(1H, s) |
| I-2<br>B | Solid;<br>m.p.: 70–71° C. | 3.88(3H, s),<br>6.57(1H, d, J=2Hz),<br>6.7–7.7(4H, complex),<br>7.44(1H, d, J=2Hz),<br>9.09(1H, s) |
| I-3<br>B | Solid;<br>m.p.: 103–104° C. | 3.89(3H, s),<br>6.58(1H, d, J=2Hz),<br>6.8–7.7(5H, complex),<br>9.09(1H, s) |
| I-5<br>B | Solid;<br>m.p.: 75–77° C. | 2.4(3H, s),<br>6.8–7.8(6H, complex),<br>9.6(1H, brs) |
| I-6<br>C | Solid;<br>m.p.: 119–120° C. | 4.38–4.90(1H, br),<br>7.28(1H, d, J=2Hz),<br>7.5–7.3(4H, complex),<br>7.63(1H, d, J=2Hz) |
| I-7<br>A | Solid;<br>m.p.: 141–143° C. | 3.04(6H, s),<br>6.17(1H, d, J=2Hz),<br>6.8–7.8(4H, complex),<br>7.21(1H, d, J=2Hz),<br>10.02(1H, s) |

TABLE 5

| Compound No.[c] | Properties | NMR[d] 60MHz, δ |
|---|---|---|
| I-8<br>A | Solid;<br>m.p.: 96–99° C. | 2.50(3H, s),<br>6.88(1H, d, J=2Hz),<br>7.0–7.7(4H, complex),<br>7.66(1H, d, J=2Hz),<br>9.40(1H, s) |
| I-9<br>A | Solid;<br>m.p.: 80–82° C. | 3.05(3H, s), 4.52(2H, s),<br>6.18(1H, d, J=2Hz),<br>6.7–7.6(10H, complex),<br>9.83(1H, s) |
| I-10<br>D | Solid;<br>m.p.: 66–68° C. | 2.90(3H, s),<br>5.3(1H, brs),<br>6.11(1H, s),<br>6.7(1H, brs),<br>7.0–8.0(5H, complex) |
| I-11<br>B | Solid;<br>m.p.: 80–83° C. | 7.1(1H, d, J=9Hz),<br>7.2–7.5(4H, complex),<br>7.8(1H, d, J=9Hz),<br>9.6(1H, br) |
| I-12<br>C | Solid;<br>m.p.: 145–147° C. | 3.80(3H, s),<br>7.1–7.6(4H, complex),<br>7.46(1H, d, J=8Hz),<br>7.76(1H, d, J=8Hz),<br>COOH was unclear |
| I-13<br>B | Solid;<br>m.p.: 88–90° C. | 6.8–7.6(5H, complex),<br>7.6–8.2(2H, complex),<br>10.17(1H, s) |

TABLE 6

| Compound No.[c] | Properties | NMR[d] 60MHz, δ |
|---|---|---|
| I-22<br>A | Solid;<br>m.p.: 93–95° C. | 4.44(2H, q, J=8Hz),<br>6.68(1H, d, J=2Hz),<br>6.9–7.3(5H, complex),<br>9.23(1H, s) |
| I-24<br>B | Solid;<br>m.p.: 80–83° C. | 3.72(3H, s),<br>3.83(3H, s),<br>6.3–6.9(3H, complex),<br>6.49(1H, d, J=2Hz),<br>6.9–7.5(1H, mult.),<br>7.40(1H, d, J=2Hz),<br>9.19(1H, s) |
| I-26<br>B | Solid;<br>m.p.: 93–95° C. | 2.33(3H, s),<br>3.83(3H, s),<br>6.49(1H, d, J=2Hz),<br>6.6–7.3(4H, complex),<br>7.40(1H, d, J=2Hz),<br>10.02 (1H, s) |
| I-27<br>B | Solid;<br>m.p.: 108–109° C. | 3.83(3H, s),<br>6.51(1H, d, J=2Hz),<br>6.7–7.4(4H, complex),<br>7.37(1H, d, J=2Hz),<br>10.07(1H, s) |
| I-30<br>A | Viscous substance | 1.22(3H, t, J=7Hz),<br>3.51(2H, q, H=7Hz),<br>4.55(2H, s),<br>6.21(1H, d, J=2Hz),<br>6.7–7.8(10H, complex),<br>9.68(1H, s) |

TABLE 7

| Compound No.[c] | Properties | NMR[d] 60MHz, δ |
|---|---|---|
| I-33<br>B | Solid;<br>m.p.: 125–127° C. | 3.90(3H, s),<br>6.59(1H, d, J=2Hz),<br>6.9–7.7(4H, complex),<br>9.06(1H, s) |
| I-34<br>B | Solid;<br>m.p.: 118–120° C. | 3.91(3H, s),<br>6.68(1H, d, J=2Hz),<br>7.0–7.7(4H, complex),<br>8.81(1H, s) |
| I-35<br>B | Solid;<br>m.p.: 136–137° C. | 3.90(3H, s),<br>6.62(1H, d, J=2Hz),<br>7.0–7.7(4H, complex),<br>9.19(1H, s) |

Note:
[c]"A" represents the step A (synthesis by addition of a carbon dioxide gas after metallation);
"B" represents the step B (synthesis by hydrolysis of a cyano group);
"C" represents the step C (synthesis by hydrolysis of an ester group); and
"D" represents the step D (synthesis by hydrocracking or hydrogenolysis of a benzyl group).
[d]As to solvents for NMR measurements, the compounds (I-6) and (I-12) were measured using dimethyl sulfoxide deuteride (DMSO-$d_6$), and the other compounds were measured using chloroform deuteride ($CDCl_3$).

Next, Formulation Examples and Experimental Examples are shown below. However, as readily understood by those skilled in the art, carriers (diluents), auxiliaries or adjuvants and mixing ratios therebetween, and effective ingredients of the formulations as shown in these Examples, can be varied over a wide range without departing from the sprits of the present invention.

Formulation Example 1

Dusting Powder

| | |
|---|---|
| Compound No. (I-1) | 3 parts by weight |
| Clay | 40 parts by weight |
| Talc | 57 parts by weight |

The above-mentioned components were mixed and pulverized together. The obtained product was used as a dusting powder.

Formulation Example 2

Water-dispersible Powder

| | |
|---|---|
| Compound No. (I-1) | 50 parts by weight |
| Lignosulfonate | 5 parts by weight |
| Alkyl sulfonate | 3 parts by weight |
| Diatomite | 42 parts by weight |

The above-mentioned components were mixed and pulverized together. The thus obtained product was used as a water-dispersible powder by diluting with water.

Formulation Example 3

Granules

| | |
|---|---|
| Compound No. (I-6) | 5 parts by weight |
| Bentonite | 43 parts by weight |
| Clay | 45 parts by weight |
| Lignosulfonate | 7 parts by weight |

The above-mentioned components were homogeneously mixed together. The obtained mixture was further kneaded by adding water thereto. The kneaded material was formed into granules by using an ordinary extrusion-type granulation, and then dried.

Formulation Example 4

Emulsion

| | |
|---|---|
| Compound No. (I-27) | 20 parts by weight |
| Polyoxyethylene alkylaryl ether | 10 parts by weight |
| Polyoxyethylene sorbitan monolaurate | 3 parts by weight |
| Xylene | 67 parts by weight |

The above-mentioned components were homogeneously mixed together to prepare an emulsion.

Experimental Example 1

Experiment for Determination of Control Effect on Gray Mold of Kidney Beans (*Phaseolus vulgaris*)

A water-dispersible powder-type formulation as shown in the above Formulation Example 2, was diluted with water to prepare a suspension having a predetermined concentration (1,000 mg/liter), and the diluted formulation was sprayed over leaves of kidney bean (cultivar: Honkintoki) at the first true leaf stage which was cultivated using an unglazed pot (about 3-inch pot) having a diameter of 9 cm, in such an amount corresponding to 100 liters/10a. After the sprayed leaves were air-dried, two circular cut pieces (diameter: 4 mm) of potato-dextrose agar in which *Botrytis cinerea* was preliminarily cultivated at 20° C. for 3 days, were directly attached to a central portion of each leaf. The inoculated leaves were maintained at 20 to 23° C. under a high-humidity condition. Three days after the inoculation, the disease index of inflected leaves by gray mold was determined according to the following examination criteria with respect to four points per one test area. Further, the preventive value was calculated from an average index of the treated areas according to the following formula.

Examination Criteria

| Index | Percentage (%) of infection area to non-treated area |
|---|---|
| 0 | 0 |
| 1 | less than 10% |
| 2 | not less than 10% and less than 20% |
| 3 | not less than 20% and less than 30% |
| 4 | not less than 30% and less than 70% |
| 5 | not less than 70% |

Preventive value (%) = [1-(Index of treated leaves)/(Index of non-treated leaves)] × 100

For example, the compound (I-1), the compound (I-6), the compound (I-27), the compound (I-30), etc., showed a preventive value of not less than 70% when the formulations composed of the respective compounds were sprayed in an amount of 1 kg/ha.

Experimental Example 2

Experiment for Determination of Control Effect on Powdery Mildew of Wheat

A water-dispersible powder-type formulation as shown in the above Formulation Example 2, was diluted with water to prepare a suspension having a predetermined concentration (1,000 mg/liter), and the diluted formulation was sprayed over wheat plants (cultivar: Norrin No. 64) at the second leaf stage which were cultivated using a rectangular plastic pot (6.4 cm×6.4 cm), in an amount of 100 liters/10a. After the sprayed wheat plants were air-dried, the spores of powdery mildew were inoculated to the plants. Thereafter, the inoculated wheat plants were maintained in a green house. Seven days after the inoculation, the disease index of infected leaves by powdery mildew was examined. Further, the preventive value was calculated according to the following formula.

Examination Criteria

| Index | Percentage (%) of infected area |
|---|---|
| 0 | No infection |
| 0.5 | less than 1% |
| 1 | not less than 1% and less than 5% |
| 2 | not less than 5% and less than 10% |
| 3 | not less than 10% and less than 30% |
| 4 | not less than 30% and less than 50% |
| 5 | not less than 50% |

Preventive value (%) = [1-(Index of sprayed area) ÷ (Index of non-sprayed area)] × 100

For example, the compound (I-1), the compound (I-2), the compound (I-3), the compound (I-5), the compound (I-11), the compound (I-22), the compound (I-26), the compound (I-34), etc., showed a preventive value of not less than 80% when the formulations composed of the respective compounds were sprayed in an amount of 1 kg/ha.

Experimental Example 3

Experiment for Determination of Control Effect on Brown Leaf Rust of Wheat

A water-dispersible powder-type formulation as shown in the above Formulation Example 2, was diluted with water to prepare a suspension having a predetermined concentration (1,000 mg/liter), and the diluted formulation was sprayed over wheat plants (cultivar: Norrin No. 64) at the second leaf stage which were cultivated using a rectangular plastic pot (6.4 cm×6.4 cm), in an amount of 100 liters/10a. After the sprayed wheat plants were air-dried, the suspension of spores of brown rust was inoculated to the plants. Thereafter, the inoculated wheat plants were maintained for 24 hours under a high-humidity condition, and then maintained in a green house. Ten to fourteen days after the inoculation, the disease index of brown rust on the wheat leaves was examined. Further, the preventive value was calculated according to the following formula.

Examination Criteria

| Index | Percentage (%) of severity by brown rust as prescribed by Peterson, et al.* |
|---|---|
| 0 | No infection |
| 0.5 | less than 1% |
| 1 | not less than 1% and less than 5% |
| 2 | not less than 5% and less than 10% |
| 3 | not less than 10% and less than 30% |
| 4 | not less than 30% and less than 50% |
| 5 | not less than 50% |

Note:
*"Test method for disinfectants applied to rice, wheat, etc., in farm", published by Japan Plant Epidemic Prevention Association, page 111 (1990).
Preventive value (%) = [1-(Index of sprayed area) ÷ (Index of non-sprayed area)] × 100

For example, the compound (I-3), the compound (I-5), the compound (I-22), etc., showed a preventive value of not less than 70% when the formulations composed of the respective compounds were sprayed in an amount of 1 kg/ha.

INDUSTRIAL APPLICABILITY

In accordance with the present invention, 6-(unsubstituted or substituted) phenoxy picolinic acid represented by the above general formula, is useful as an effective ingredient of agricultural or horticultural fungicides which can show an excellent control effect on extensive plant diseases.

What is claimed is:
1. 6-(unsubstituted or substituted) phenoxy picolinic acid represented by the general formula (I-a):

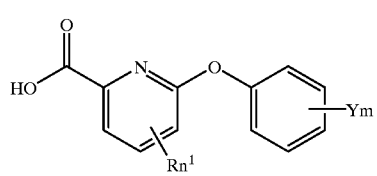

(I-a)

wherein
  R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;
  $n^1$ is an integer of 1 to 3;
  Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^1$ are not less than 2, Rs and Ys may be the same or different, respectively.

2. A process for producing 6-(unsubstituted or substituted) phenoxy picolinic acid represented by the general formula (I-b), which process comprises metallizing a 2-halogeno-6-(unsubstituted or substituted) phenoxy pyridine derivative represented by the general formula (III) to obtain 2-(metal-substituted)-6-(unsubstituted or substituted) phenoxy pyridine derivative represented by the general formula (II), reacting the obtained pyridine derivative (II) with carbon dioxide, and then subjecting the reaction product to proton-substitution

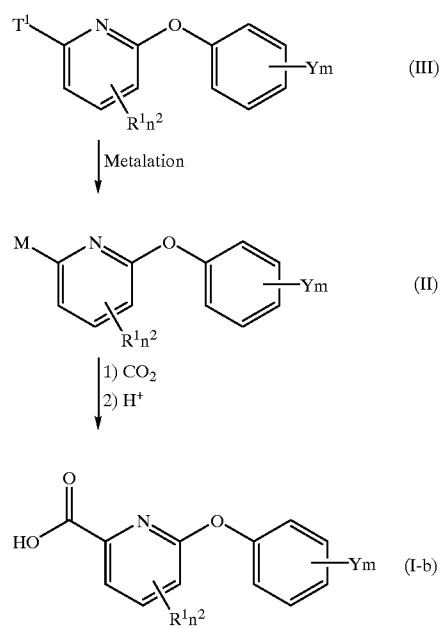

wherein $R^1$ is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a di($C_1$ to $C_4$) alkylamino group or a $C_7$ to $C_8$ aralkyl ($C_1$ to $C_4$ alkyl) amino group;

$n^2$ is an integer of 0 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m and $n^2$ are not less than 2, $R^1$s and Ys may be the same or different, respectively;

$T^1$ is a halogen atom; and

M is alkali metal, alkali earth metal-Q wherein Q is a halogen atom, or ½(Cu-alkali metal.

3. A process for producing 6-(unsubstituted or substituted) phenoxy picolinic acid represented by the general formula (I-a), which process comprises hydrolyzing a 2-cyano-6-(unsubstituted or substituted) phenoxy pyridine derivative represented by the general formula (IV)

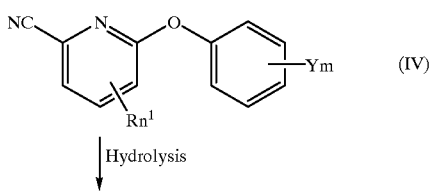

Hydrolysis

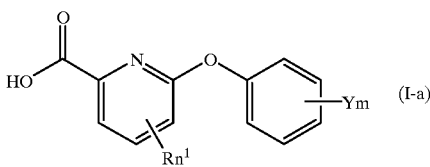

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^1$ is an integer of 1 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^1$ are not less than 2, Rs and Ys may be the same or different, respectively.

4. A process for producing 6-(unsubstituted or substituted) phenoxy picolinic acid represented by the general formula (I-a), which process comprises hydrolyzing a 6-(unsubstituted or substituted) phenoxy picolinic acid ester represented by the general formula (V)

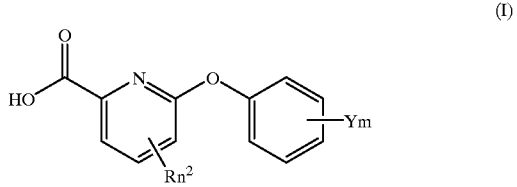

Hydrolysis

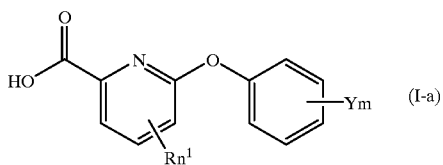

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^1$ is an integer of 1 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m and $n^1$ are not less than 2, Rs and Ys may be the same or different, respectively; and B is a lower alkyl group.

5. An agricultural or horticultural fungicide containing 6-(unsubstituted or substituted) phenoxy picolinic acid represented by the general formula (I), as an effective ingredient

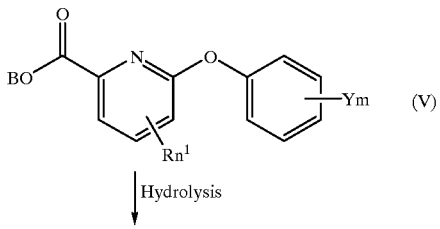

wherein

R is a halogen atom, a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ alkylamino group, a di($C_1$ to $C_4$ alkyl)amino group or a $C_7$ to $C_8$ aralkyl($C_1$ to $C_4$ alkyl)amino group;

$n^2$ is an integer of 0 to 3;

Y is a $C_1$ to $C_4$ alkyl group, a $C_1$ to $C_4$ haloalkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom; and m is an integer of 0 to 5, and when m and $n^2$ are not less than 2, Rs and Ys may be the same or different, respectively.

\* \* \* \* \*